(12) United States Patent
Kim

(10) Patent No.: US 12,260,840 B2
(45) Date of Patent: Mar. 25, 2025

(54) DISPLAY DEVICE AND DRIVING METHOD OF THE SAME

(71) Applicant: Samsung Display Co., Ltd., Yongin-si (KR)

(72) Inventor: Chul Kim, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

(21) Appl. No.: 18/525,591

(22) Filed: Nov. 30, 2023

(65) Prior Publication Data

US 2024/0290298 A1 Aug. 29, 2024

(30) Foreign Application Priority Data

Feb. 27, 2023 (KR) .................. 10-2023-0025740

(51) Int. Cl.
*G09G 5/10* (2006.01)
*A61B 5/021* (2006.01)
*G06F 21/32* (2013.01)

(52) U.S. Cl.
CPC .............. *G09G 5/10* (2013.01); *A61B 5/021* (2013.01); *G06F 21/32* (2013.01); *G09G 2320/0626* (2013.01)

(58) Field of Classification Search
CPC ... A61B 5/6898; A61B 5/021; A61B 5/02108; A61B 5/02427; A61B 5/0059; G06V 40/1318; G06V 40/13; G06V 40/1365; G06V 40/15; G06V 40/70; G06V 40/193; G06F 3/042; G06F 21/32; G06F 2203/011; G06F 3/041; G06F 3/0488; G06F 3/04883; G06F 3/0412; G06F 3/0416; H10K 59/13; H10K 59/65; H10K 59/60

See application file for complete search history.

(56) References Cited

U.S. PATENT DOCUMENTS

| | | | |
|---|---|---|---|
| 10,398,324 B2 | 9/2019 | Mukkamala et al. | |
| 11,423,684 B2 | 8/2022 | Kim et al. | |
| 2022/0047170 A1* | 2/2022 | Seomoon | A61B 5/14552 |

FOREIGN PATENT DOCUMENTS

| | | | | |
|---|---|---|---|---|
| CN | 112869720 A | * | 6/2021 | ......... A61B 5/02108 |
| KR | 10-2020-0118270 A | | 10/2020 | |
| KR | 10-2493607 B1 | | 2/2023 | |

OTHER PUBLICATIONS

CN-112869720-A (Year: 2021).*

* cited by examiner

*Primary Examiner* — Sanjiv D. Patel

(74) *Attorney, Agent, or Firm* — Womble Bond Dickinson (US) LLP

(57) ABSTRACT

A display device includes: a display panel including: a plurality of pixels, each including a light emitting element; and a plurality of sensors, each including a light sensing element; a panel driving circuit to drive the plurality of pixels; a readout circuit to receive a sensing signal from the plurality of sensors; and a controller to control the panel driving circuit and the readout circuit. The controller is to: control the panel driving circuit to set a luminance of pixels in an emission area from among the plurality of pixels to a first luminance level in a fingerprint sensing mode; and control the panel driving circuit to set the luminance of the pixels in the emission area to a second luminance level in a blood pressure sensing mode, and the second luminance level is higher than the first luminance level.

20 Claims, 17 Drawing Sheets

DISPLAY DEVICE AND DRIVING METHOD OF THE SAME

CROSS-REFERENCE TO RELATED APPLICATION

This application claims priority to and the benefit of Korean Patent Application No. 10-2023-0025740, filed on Feb. 27, 2023, in the Korean Intellectual Property Office, the entire disclosure of which is incorporated by reference herein.

BACKGROUND

1. Field

Aspects of embodiments of the present disclosure relate to a display device capable of recognizing biometric information and recognizing a touch.

2. Description of the Related Art

A display device provides various functions to provide information to a user by displaying an image, or to communicate organically with the user, such as detecting a user input. Nowadays, display devices may include a function to detect the user's biometric information. Biometric information recognition schemes include a capacitive scheme that detects a change in capacitance between electrodes, an optical scheme that detects incident light by using an optical sensor, and an ultrasonic scheme that detects vibrations by using a piezoelectric material or the like.

The above information disclosed in this Background section is for enhancement of understanding of the background of the present disclosure, and therefore, it may contain information that does not constitute prior art.

SUMMARY

Embodiments of the present disclosure are directed to a display device including a sensor capable of detecting biometric information.

Embodiments of the present disclosure are directed to a method for driving a display device capable of improving the sensing performance of fingerprint sensing and blood pressure sensing.

According to one or more embodiments of the present disclosure, a display device includes: a display panel including: a plurality of pixels, each of the plurality of pixels including a light emitting element; and a plurality of sensors, each of the plurality of sensors including a light sensing element; a panel driving circuit configured to drive the plurality of pixels; a readout circuit configured to receive a sensing signal from the plurality of sensors; and a controller configured to control the panel driving circuit and the readout circuit. The controller is configured to: control the panel driving circuit to set a luminance of pixels in an emission area from among the plurality of pixels to a first luminance level in a fingerprint sensing mode; and control the panel driving circuit to set the luminance of the pixels in the emission area to a second luminance level in a blood pressure sensing mode, and the second luminance level is higher than the first luminance level.

In an embodiment, during a first emission and blood pressure sensing period of the blood pressure sensing mode, the controller may be configured to measure a blood pressure of a user based on a readout signal received from the readout circuit.

In an embodiment, when the blood pressure cannot be sufficiently measured based on the readout signal during the first emission and blood pressure sensing period, the controller may be configured to change the luminance of the pixels in the emission area to a luminance level higher than the second luminance level during a second emission and blood pressure sensing period of the blood pressure sensing mode.

In an embodiment, during the second emission and blood pressure sensing period of the blood pressure sensing mode, the controller may be configured to measure the blood pressure of the user based on the readout signal received from the readout circuit.

In an embodiment, during a first emission and fingerprint sensing period of the fingerprint sensing mode, the controller may be configured to perform an authentication process by comparing a readout signal received from the readout circuit with a pre-stored fingerprint signal.

In an embodiment, when the readout signal does not match the pre-stored fingerprint signal, the controller may be configured to change the luminance of the pixels in the emission area into a luminance level higher than the first luminance level of the first emission and fingerprint sensing period.

In an embodiment, during a fingerprint sensing time in the fingerprint sensing mode, the readout circuit may be configured to receive a sensing signal from sensors in a fingerprint sensing area from among the plurality of sensors, and during a blood pressure sensing time in the blood pressure sensing mode, the readout circuit may be configured to receive the sensing signal from sensors in a blood pressure sensing area from among the plurality of sensors. The blood pressure sensing time may be longer than the fingerprint sensing time.

In an embodiment, during the fingerprint sensing mode, the controller may be configured to receive a sensing signal from sensors in a fingerprint sensing area from among the plurality of sensors, and during the blood pressure sensing mode, the controller may be configured to receive the sensing signal from sensors in a blood pressure sensing area from among the plurality of sensors.

In an embodiment, in the fingerprint sensing mode, sizes and shapes of the emission area and the fingerprint sensing area may be the same as each other.

In an embodiment, in the blood pressure sensing mode, sizes and shapes of the emission area and the blood pressure sensing area may be different from each other.

In an embodiment, in the blood pressure sensing mode, the emission area may have a circle shape having a radius, and the blood pressure sensing area may have a ring shape surrounding the emission area.

In an embodiment, each of the plurality of sensors may further include: a first transistor connected between a reset voltage line and a first sensing node; a second transistor connected between a sensor driving voltage line and a second sensing node, and including a gate electrode connected to the first sensing node; and a third transistor connected between the second sensing node and a readout line, and including a gate electrode configured to receive a sensor scan signal.

In an embodiment, the display panel may further include: a base layer; a circuit layer on the base layer; and an element layer on the circuit layer, and including the light emitting element and the light sensing element.

According to one or more embodiments of the present disclosure, a display device includes: a display panel including: a plurality of pixels, each of the plurality of pixels including a light emitting element; and a plurality of sensors, each of the plurality of sensors including a light sensing element; a panel driving circuit configured to drive the plurality of pixels; a readout circuit configured to receive a sensing signal from the plurality of sensors; and a controller configured to control the panel driving circuit and the readout circuit. The controller is configured to: control the panel driving circuit to set a luminance of pixels in an emission area from among the plurality of pixels to a luminance level in a blood pressure sensing mode; and control the readout circuit to receive a sensing signal from sensors in a blood pressure sensing area from among the plurality of sensors. Sizes and shapes of the emission area and the blood pressure sensing area are different from each other.

In an embodiment, in the blood pressure sensing mode, the emission area may have a circle shape having a radius, and the blood pressure sensing area may have a ring shape surrounding the emission area.

In an embodiment, the controller may be configured to control the panel driving circuit to set the luminance of the pixels in the emission area to a first luminance level in a fingerprint sensing mode, and control the panel driving circuit to set the luminance of the pixels in the emission area to a second luminance level in a blood pressure sensing mode, and the second luminance level may be higher than the first luminance level.

According to one or more embodiments of the present disclosure, an operating method of a display device including a display panel including a plurality of pixels and a plurality of sensors, includes: determining an operating mode from among a fingerprint sensing mode and a blood pressure sensing mode; controlling a luminance of pixels in an emission area from among the plurality of pixels to a first luminance level, when the operating mode is the fingerprint sensing mode; and controlling the luminance of the pixels in the emission area to a second luminance level, when the operating mode is the blood pressure sensing mode. The second luminance level is higher than the first luminance level.

In an embodiment, the method may further include: authenticating a fingerprint based on a signal received from sensors in a fingerprint sensing area from among the plurality of sensors, when the operating mode is the fingerprint sensing mode; and measuring blood pressure of a user based on a signal received from sensors in a blood pressure sensing area from among the plurality of sensors, when the operating mode is the blood pressure sensing mode.

In an embodiment, the method may further include changing the luminance of the pixels in the emission area to a level higher than the second luminance level, when the blood pressure of the user cannot be sufficiently measured based on the signal received from the sensors in the blood pressure sensing area.

In an embodiment, sizes and shapes of the emission area and the blood pressure sensing area may be different from each other.

BRIEF DESCRIPTION OF THE DRAWINGS

The above and other aspects and features of the present disclosure will be more clearly understood from the following detailed description of the illustrative, non-limiting embodiments with reference to the accompanying drawings.

DETAILED DESCRIPTION

Figure 1:
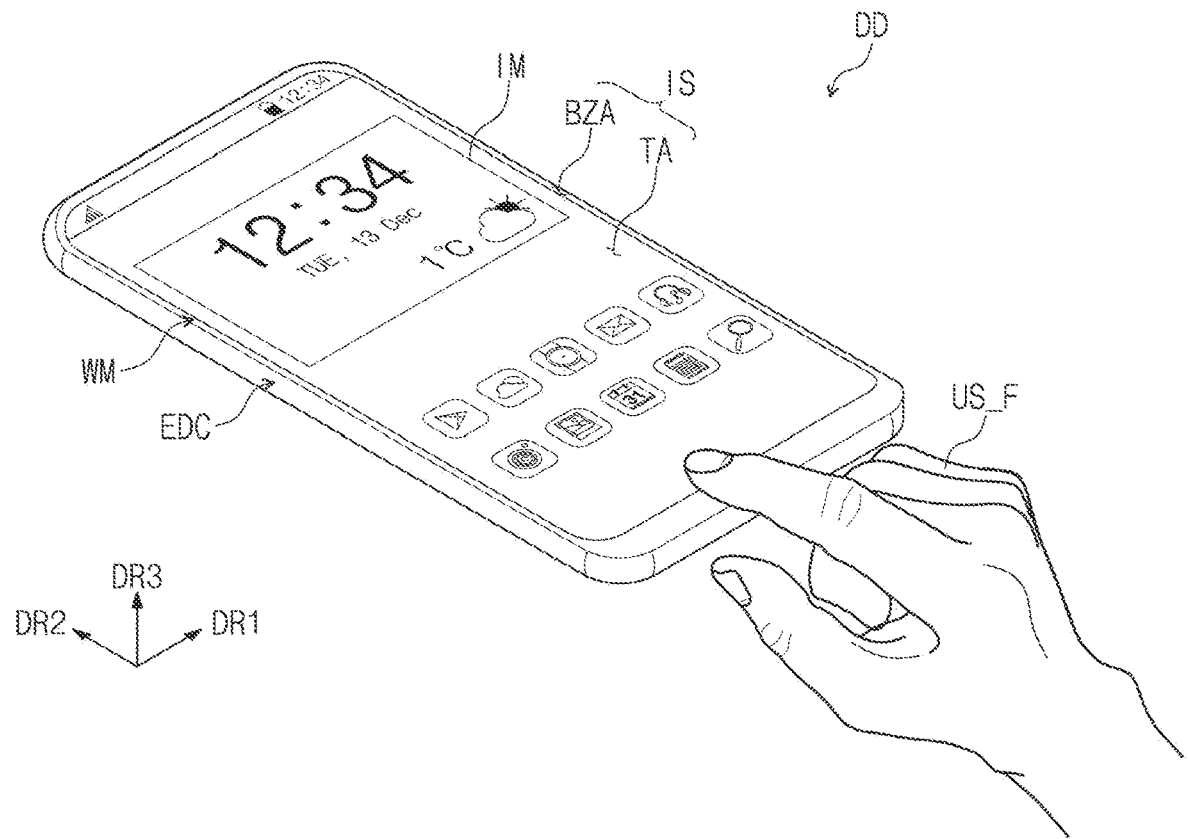
FIG. 1 is a perspective view of a display device, according to an embodiment of the present disclosure.

Hereinafter, embodiments will be described in more detail with reference to the accompanying drawings, in which like reference numbers refer to like elements throughout. The present disclosure, however, may be embodied in various different forms, and should not be construed as being limited to only the illustrated embodiments herein. Rather, these embodiments are provided as examples so that this disclosure will be thorough and complete, and will fully convey the aspects and features of the present disclosure to those skilled in the art. Accordingly, processes, elements, and techniques that are not necessary to those having ordinary skill in the art for a complete understanding of the aspects and features of the present disclosure may not be described. Unless otherwise noted, like reference numerals denote like elements throughout the attached drawings and the written description, and thus, redundant description thereof may not be repeated.

When a certain embodiment may be implemented differently, a specific process order may be different from the described order. For example, two consecutively described processes may be performed at the same or substantially at the same time, or may be performed in an order opposite to the described order.

In the drawings, the relative sizes, thicknesses, and ratios of elements, layers, and regions may be exaggerated and/or simplified for clarity. Spatially relative terms, such as "beneath," "below," "lower," "under," "above," "upper," and the like, may be used herein for ease of explanation to describe one element or feature's relationship to another element(s) or feature(s) as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly.

In the figures, the x-axis, the y-axis, and the z-axis are not limited to three axes of the rectangular coordinate system, and may be interpreted in a broader sense. For example, the x-axis, the y-axis, and the z-axis may be perpendicular to or substantially perpendicular to one another, or may represent different directions from each other that are not perpendicular to one another.

It will be understood that, although the terms "first," "second," "third," etc., may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

It will be understood that when an element or layer is referred to as being "on," "connected to," or "coupled to" another element or layer, it can be directly on, connected to, or coupled to the other element or layer, or one or more intervening elements or layers may be present. Similarly, when a layer, an area, or an element is referred to as being "electrically connected" to another layer, area, or element, it may be directly electrically connected to the other layer, area, or element, and/or may be indirectly electrically connected with one or more intervening layers, areas, or elements therebetween. In addition, it will also be understood that when an element or layer is referred to as being "between" two elements or layers, it can be the only element or layer between the two elements or layers, or one or more intervening elements or layers may also be present.

The terminology used herein is for the purpose of describing particular embodiments and is not intended to be limiting of the present disclosure. As used herein, the singular forms "a" and "an" are intended to include the plural forms as well, unless the context clearly indicates otherwise. It will be further understood that the terms "comprises," "comprising," "includes," "including," "has," "have," and "having," when used in this specification, specify the presence of the stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. For example, the expression "A and/or B" denotes A, B, or A and B. Expressions such as "at least one of," when preceding a list of elements, modify the entire list of elements and do not modify the individual elements of the list. For example, the expression "at least one of a, b, or c," "at least one of a, b, and c," and "at least one selected from the group consisting of a, b, and c" indicates only a, only b, only c, both a and b, both a and c, both b and c, all of a, b, and c, or variations thereof.

As used herein, the term "substantially," "about," and similar terms are used as terms of approximation and not as terms of degree, and are intended to account for the inherent variations in measured or calculated values that would be recognized by those of ordinary skill in the art. Further, the use of "may" when describing embodiments of the present disclosure refers to "one or more embodiments of the present disclosure." As used herein, the terms "use," "using," and "used" may be considered synonymous with the terms "utilize," "utilizing," and "utilized," respectively.

Unless otherwise defined, all terms (including technical and scientific terms) used herein have the same meaning as commonly understood by one of ordinary skill in the art to which the present disclosure belongs. It will be further understood that terms, such as those defined in commonly used dictionaries, should be interpreted as having a meaning that is consistent with their meaning in the context of the relevant art and/or the present specification, and should not be interpreted in an idealized or overly formal sense, unless expressly so defined herein.

Figure 2:
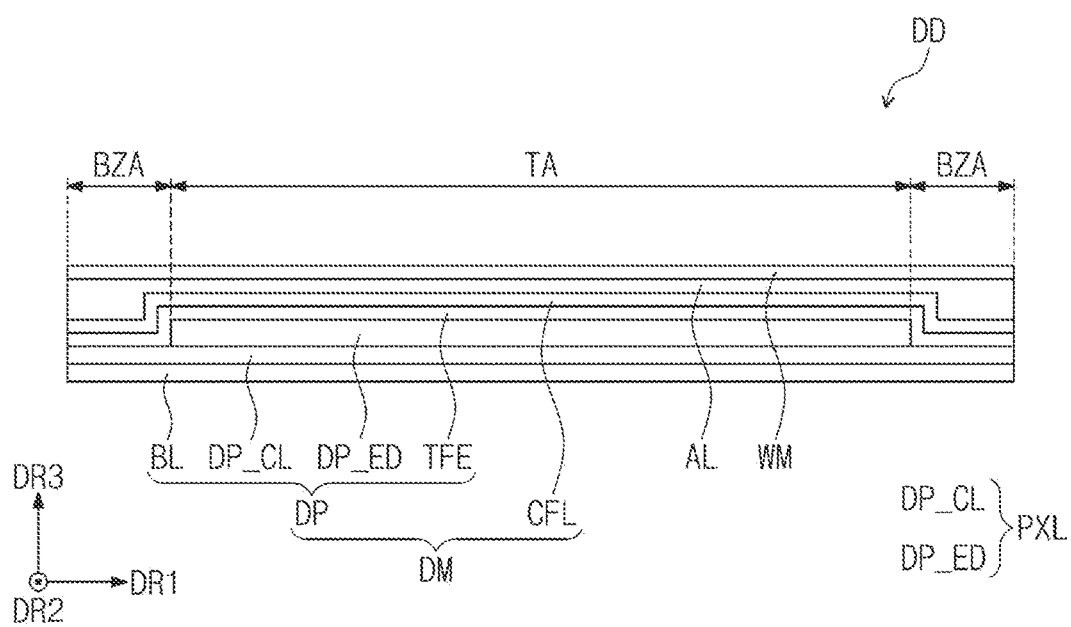
FIG. 2 is a cross-sectional view of a display device, according to an embodiment of the present disclosure.

FIG. 1 is a perspective view of a display device DD, according to an embodiment of the present disclosure. FIG. 2 is a cross-sectional view of the display device DD, according to an embodiment of the present disclosure.

Referring to FIGS. 1 and 2, the display device DD may be a device that is activated depending on an electrical signal. For example, the display device DD may be a mobile phone, a tablet PC, a car navigation system, a game console, or a wearable device, but the present disclosure is not limited thereto. For convenience, FIG. 1 illustrates that the display device DD is a mobile phone.

In addition, while a rigid-type display device DD in the form of a bar shape is illustrated in FIG. 1, the present disclosure is not particularly limited thereto. For example, the display device DD may be a foldable, rollable, or slidable display device DD.

A top surface of the display device DD may be defined as a display surface IS, and may have a plane defined by a first direction DR1 and a second direction DR2. Images IM generated by the display device DD may be provided to a user through the display surface IS. Hereinafter, a normal direction that is perpendicular to or substantially perpendicular to the plane defined by the first direction DR1 and the second direction DR2 is defined as a third direction DR3. As used herein, the meaning of "when viewed from above a plane" and "in a plan view" may mean "when viewed in the third direction DR3". In other words, the plane may be parallel to or substantially parallel to a plane defined by the first and second directions DR1 and DR2.

The display surface IS may be divided into a transmission area TA and a bezel area BZA. The transmission area TA may be an area in which the images IM are displayed. The user may visually perceive the images IM through the transmission area TA. In an embodiment, the transmission area TA is illustrated in the shape of a quadrangle having corners that are rounded. However, the present disclosure is not limited thereto. The transmission area TA may have various suitable shapes, and is not limited to any particular embodiment.

The bezel area BZA is adjacent to the transmission area TA. The bezel area BZA may have a suitable color (e.g., a predetermined color). The bezel area BZA may surround (e.g., around a periphery of) the transmission area TA. Accordingly, the shape of the transmission area TA may be defined or substantially defined by the bezel area BZA. However, the present disclosure is not limited thereto. For example, the bezel area BZA may be disposed to be adjacent to only one side of the transmission area TA, or may be omitted as needed or desired.

The display device DD may sense an external input applied from the outside. The external input may include various suitable kinds of inputs that are provided from the outside of the display device DD. For example, the external input may include a contact by a part of a body, such as the user's finger US_F, as well as an external input (e.g., hovering) applied when the user's hand US_F approaches the display device DD or is adjacent to the display device DD within a suitable distance (e.g., a predetermined distance). In addition, the external input may have various suitable kinds, such as force, pressure, temperature, light, and/or the like. The external input may be provided by a separate device, for example, such as an active pen or a digitizer pen. The display device DD may detect the user's biometric information applied from the outside.

The appearance of the display device DD may be composed of a window WM and housing EDC. For example, the window WM and the housing EDC may be connected (e.g., coupled or attached) to each other, and other components of the display device DD, for example, such as a display module (e.g., a display or a touch-display) DM, may be accommodated therein.

A front surface of the window WM defines the display surface IS of the display device DD. The window WM may include an optically transparent insulating material. For example, the window WM may include glass or plastic. The window WM may include a multi-layered structure or a single layer structure. For example, the window WM may include a plurality of plastic films that are bonded to each other by an adhesive, or may have a glass substrate and a plastic film that are bonded to each other by an adhesive.

The housing EDC may include a suitable material having relatively high rigidity. For example, the housing EDC may include glass, plastic, or a metal, or may include a plurality of frames and/or plates that are composed of a combination thereof. The housing EDC may stably protect the configurations of the display device DD accommodated in the inner space from external impacts. A battery module (e.g., a battery) for supplying power used for the overall operations of the display device DD may be interposed between the display module DM and the housing EDC.

The display module DM may include a display panel DP and an anti-reflection layer CFL.

The display panel DP may be a configuration that generates or substantially generates an image. The display panel DP may be a light emitting display panel. For example, the display panel DP may be an organic light emitting display panel, an inorganic light emitting display panel, an organic-inorganic light emitting display panel, a quantum dot display panel, a micro-LED display panel, or a nano-LED display panel. Hereinafter, for convenience, the display panel DP may be described in more detail in the context of an organic light emitting display panel, but the present disclosure is not limited thereto.

The display panel DP includes a base layer BL, a pixel layer PXL, and an encapsulation layer TFE. The display panel DP according to an embodiment of the present disclosure may be a flexible display panel. However, the present disclosure is not limited thereto. For example, the display panel DP may be a foldable display panel, which is foldable with respect to a folding axis, or a rigid display panel.

The base layer BL may include a synthetic resin layer. The synthetic resin layer may be a polyimide-based resin layer, but the material thereof is not particularly limited thereto. The base layer BL may include a glass substrate, a metal substrate, an organic/inorganic composite substrate, or the like.

The pixel layer PXL is disposed on the base layer BL. The pixel layer PXL may include a circuit layer DP_CL and an element layer DP_ED. The circuit layer DP_CL is interposed between the base layer BL and the element layer DP_ED.

The circuit layer DP_CL includes at least one insulating layer, and a circuit element. Hereinafter, the insulating layer included in the circuit layer DP_CL is referred to as an "intermediate insulating layer". The intermediate insulating layer includes at least one intermediate inorganic film, and at least one intermediate organic film. The circuit element may include a pixel circuit, which is included for each of a plurality of pixels for displaying an image, and a sensor driving circuit, which is included for each of a plurality of sensors for recognizing external information. The circuit layer DP_CL may further include signal lines connected to the pixel circuit and/or the sensor driving circuit.

As an example, each of the plurality of sensors may be a fingerprint recognition sensor, a proximity sensor, an iris recognition sensor, or the like. Furthermore, each of the plurality of sensors may be an optical sensor that recognizes the biometric information in an optical scheme. According to an embodiment of the present disclosure, an external input (e.g., a user's touch), as well as biometric information (e.g., a fingerprint), may be sensed by using the plurality of sensors. Accordingly, the display device DD may not include a separate input sensing layer for sensing the external input. In this case, the thickness of the display device DD may be reduced. As a result, flexibility may be improved, and thus, the display device DD may be implemented in various suitable ways. For example, the display device DD may be implemented as a foldable, rollable, or slidable display device as described above.

The element layer DP_ED may include a light emitting element included for each of the pixels, and a light sensing element included for each of the sensors. As an example, the light sensing element may be a photodiode. The light sensing element may be a sensor that detects or responds to light reflected by a user's fingerprint. The circuit layer DP_CL and the element layer DP_ED will be described in more detail below with reference to FIG. 9.

The encapsulation layer TFE encapsulates the element layer DP_ED. The encapsulation layer TFE may include at least one organic film, and at least one inorganic film. The inorganic film may include one or more inorganic materials, and may protect the element layer DP_ED from moisture/oxygen. The inorganic film may include a silicon nitride layer, a silicon oxynitride layer, a silicon oxide layer, a titanium oxide layer, an aluminum oxide layer, or the like, but the present disclosure is not limited particularly thereto.

The organic film may include one or more organic materials, and may protect the element layer DP_ED from foreign objects, such as dust particles.

The anti-reflection layer CFL may be disposed on the display panel DP. The anti-reflection layer CFL may reduce a reflectance of external light incident from the outside of the display device DD. The anti-reflection layer CFL may be formed on the input display panel DP through one or more sequential processes, but the present disclosure is not limited thereto. For example, the anti-reflection layer CFL may include color filters, a black matrix, and a planarization layer. The color filters may have a suitable arrangement (e.g., a given or predetermined arrangement). For example, the color filters may be arranged in consideration of the emission colors of the pixels included in the display panel DP. In an embodiment, the anti-reflection layer CFL may include a black matrix and a reflection adjustment layer. The reflection adjustment layer may selectively absorb light in a partial band from among light reflected from inside the display panel DP and/or an electronic device, or incident light from the outside of the display panel DP and/or the electronic device. In an embodiment, the anti-reflection layer CFL may include (e.g., may be) a polarizing film.

The display device DD according to an embodiment of the present disclosure may further include an adhesive layer AL. The window WM may be attached to the anti-reflection layer CFL by the adhesive layer AL. The adhesive layer AL may include an optical clear adhesive, an optically clear adhesive resin, or a pressure sensitive adhesive (PSA).

Figure 3:
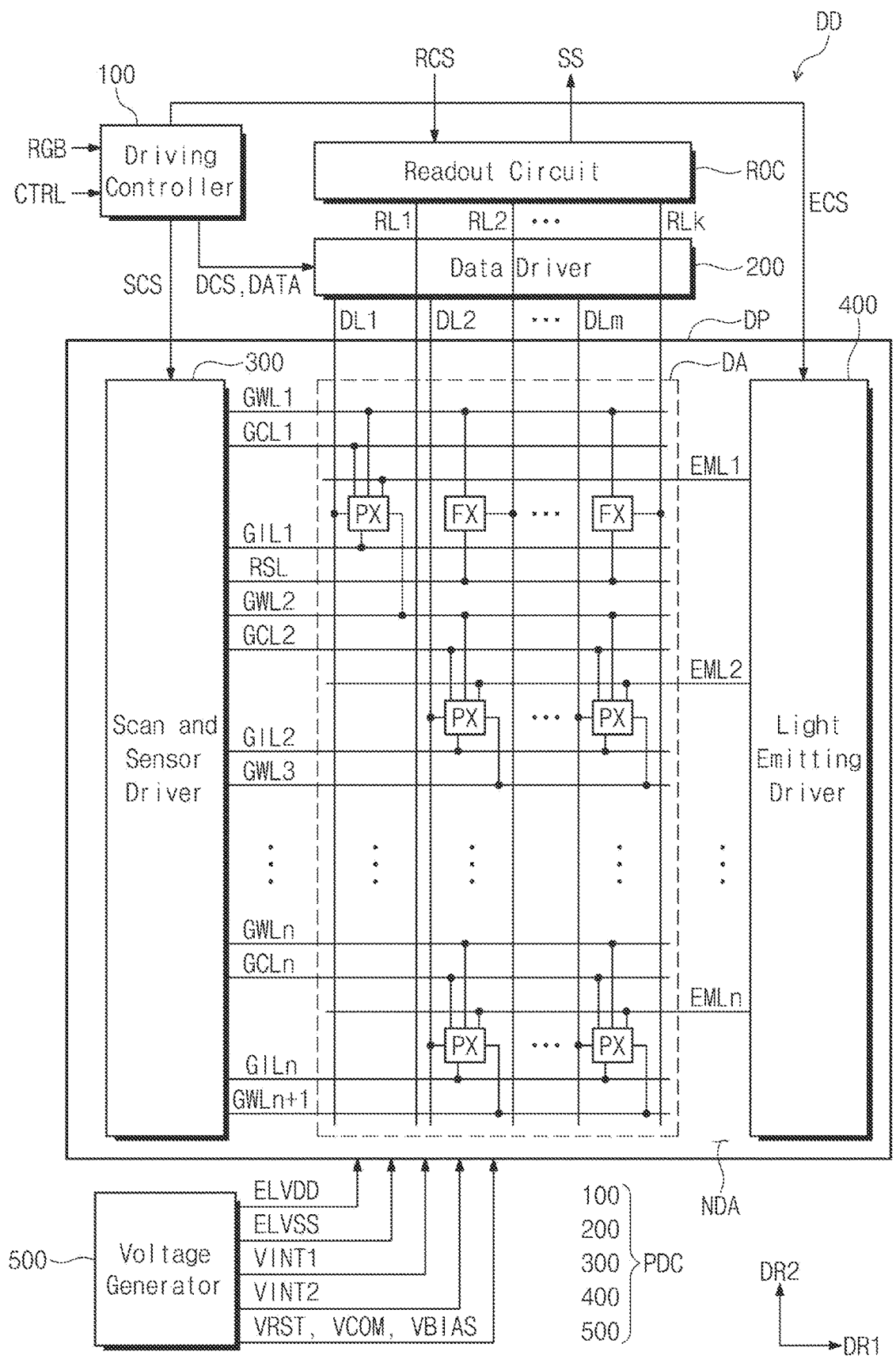
FIG. 3 is a block diagram of a display device, according to an embodiment of the present disclosure.

FIG. 3 is a block diagram of a display device, according to an embodiment of the present disclosure.

Referring to FIG. 3, the display device DD includes the display panel DP, a driving controller 100, a data driver 200, a scan and sensor driver 300, a light emitting driver 400, a readout circuit ROC, and a voltage generator 500. A panel driving circuit PDC may include the driving controller 100, the data driver 200, the scan and sensor driver 300, the light emitting driver 400, and the voltage generator 500.

The driving controller 100 receives an input image signal RGB and a control signal CTRL. The driving controller 100 generates an output image signal DATA by converting a data format of the input image signal RGB, so as to be suitable for the display panel DP and the data driver 200. The driving controller 100 outputs a scan control signal SCS, a data control signal DCS, and an emission control signal ECS.

The data driver 200 receives the data control signal DCS and the output image signal DATA from the driving controller 100. The data driver 200 converts the output image signal DATA into data signals, and then outputs the data signals to a plurality of data lines DL1 to DLm described in more detail below. The data signals refer to voltages (e.g., analog voltages) corresponding to a grayscale level of the output image signal DATA.

The voltage generator 500 generates voltages used to operate the display panel DP. In an embodiment, the voltage generator 500 generates a first driving voltage ELVDD, a second driving voltage ELVSS, a first initialization voltage VINT1, a second initialization voltage VINT2, a reset voltage VRST, a sensor driving voltage VCOM, and a bias voltage VBIAS.

The display panel DP includes scan lines GIL1 to GILn, GCL1 to GCLn, and GWL1 to GWLn+1, reset lines RSL, emission lines EML1 to EMLn, the data lines DL1 to DLm, readout lines RL1 to RLk, pixels PX, and sensors FX. Here, "n", "m", and "k" are each natural numbers.

The display panel DP may include a display area DA corresponding to the transmission area TA (e.g., see FIG. 1), and a non-display area NDA corresponding to the bezel area BZA. Pixels PX and sensors FX may be disposed in the display area DA.

The scan and sensor driver 300 and the light emitting driver 400 may be positioned in the non-display area NDA of the display panel DP.

In an embodiment, the scan and sensor driver 300 is disposed adjacent to a first side of the display area DA in the display panel DP. The scan and sensor driver 300 receives the scan control signal SCS from the driving controller 100. The scan and sensor driver 300 may output scan signals to the scan lines GIL1 to GILn, GCL1 to GCLn, and GWL1 to GWLn+1 in response to the scan control signal SCS, and may output a reset signal to the reset lines RSL. The scan lines GIL1 to GILn, GCL1 to GCLn, and GWL1 to GWLn+1 and the reset lines RSL extend from the scan and sensor driver 300 in the first direction DR1.

The light emitting driver 400 is disposed to be adjacent to a second side of the display area DA in the display panel DP. The light emitting driver 400 receives the emission control signal ECS from the driver controller 100. The light emitting driver 400 may output emission signals to the emission lines EML1 to EMLn in response to the emission control signal ECS. The emission lines EML1 to EMLn extend from the light emitting driver 400 in a direction opposite to the first direction DR1.

The scan lines GIL1 to GILn, GCL1 to GCLn, and GWL1 to GWLn, the reset lines RSL, and the emission lines EML1 to EMLn are arranged to be spaced from one another along the second direction DR2. The data lines DL1 to DLm extend from the data driver 200 in a direction opposite to the second direction DR2, and are arranged to be spaced from one another along the first direction DR1.

The plurality of pixels PX are electrically connected to the scan lines GIL1 to GILn, GCL1 to GCLn, and GWL1 to GWLn+1, the emission lines EML1 to EMLn, and the data lines DL1 to DLm. In an embodiment, each of the plurality of pixels PX may be electrically connected to four scan lines and one emission line. For example, as shown in FIG. 3, a first row of pixels may be connected to the scan lines GIL1, GCL1, GWL1, and GWL2, and the emission line EML1. A second row of pixels may be connected to the scan lines GIL2, GCL2, GWL2, and GWL3, and the emission line EML2.

Each of the plurality of pixels PX includes a light emitting element ED (e.g., see FIG. 5), and a pixel circuit PXC for controlling the emission of the light emitting element ED. The pixel circuit PXC may include one or more transistors, and one or more capacitors. The scan and sensor driver 300 and the light emitting driver 400 may include transistors formed through the same or substantially the same process as those of the pixel circuit PXC.

Each of the plurality of pixels PX receives the first driving voltage ELVDD, the second driving voltage ELVSS, the first initialization voltage VINT1, and the second initialization voltage VINT2 from the voltage generator 500.

Each of the sensors FX includes a light sensing element OPD (e.g., see FIG. 7) and a sensor driving circuit SDC. The sensor driving circuit SDC may include transistors formed through the same or substantially the same process as those of the pixel circuit PXC.

Each of the sensors FX may be connected to one corresponding scan line from among the scan lines GWL1 to GWLn, and one corresponding readout line from among the readout lines RL1 to RLk. The sensors FX may be connected to the reset line RSL in common. In the present embodiment, the number of sensors FX is less than the number of pixels PX. However, the present disclosure is not limited thereto. In an embodiment, the number of sensors FX in the display panel DP may be greater than or equal to the number of pixels PX. In an embodiment, the number of readout lines RL1 to RLk is less than the number of data lines DL1 to DLm. In other words, k<m. However, the present disclosure is not limited thereto. In an embodiment, the number of readout lines RL1 to RLk disposed on the display panel DP may be greater than or equal to the number of data lines DL1 to DLm.

The readout circuit ROC receives the readout control signal RCS. The readout circuit ROC may receive a sensing signal from the readout lines RL1 to RLk in response to the readout control signal RCS, and may output a readout signal SS.

Although FIG. 3 shows that the readout circuit ROC receives the readout control signal RCS from the outside (e.g., from an application processor, a graphic processor, a main processor, or the like), and outputs the readout signal SS to the outside, the present disclosure is not limited thereto. In an embodiment, the readout circuit ROC may receive the readout control signal RCS from the driving controller 100, and may output the readout signal SS to the driving controller 100.

In an embodiment, the sensors FX and the readout circuit ROC may operate in a blood pressure sensing mode, a fingerprint sensing mode, and a touch sensing mode. In the blood pressure sensing mode, the readout signal SS output from the readout circuit ROC may be a blood pressure sensing signal corresponding to the user's blood pressure. In the fingerprint sensing mode, the readout signal SS output from the readout circuit ROC may be a fingerprint sensing signal corresponding to the user's fingerprint. In the touch sensing mode, the readout signal SS output from the readout circuit ROC may be a signal indicating the user's touch location.

In the example shown in FIG. 3, the scan and sensor driver 300 is arranged to face the light emitting driver 400 with the pixels PX interposed therebetween, but the present disclosure is not limited thereto. For example, the scan and sensor driver 300 and the light emitting driver 400 may be arranged to be side by side one another to be adjacent to one of the first side surface or the second side surface of the display area DA in the display panel DP. In an embodiment, the scan and sensor driver 300 and the light emitting driver 400 may be integrated with each other into one circuit.

Figure 4:
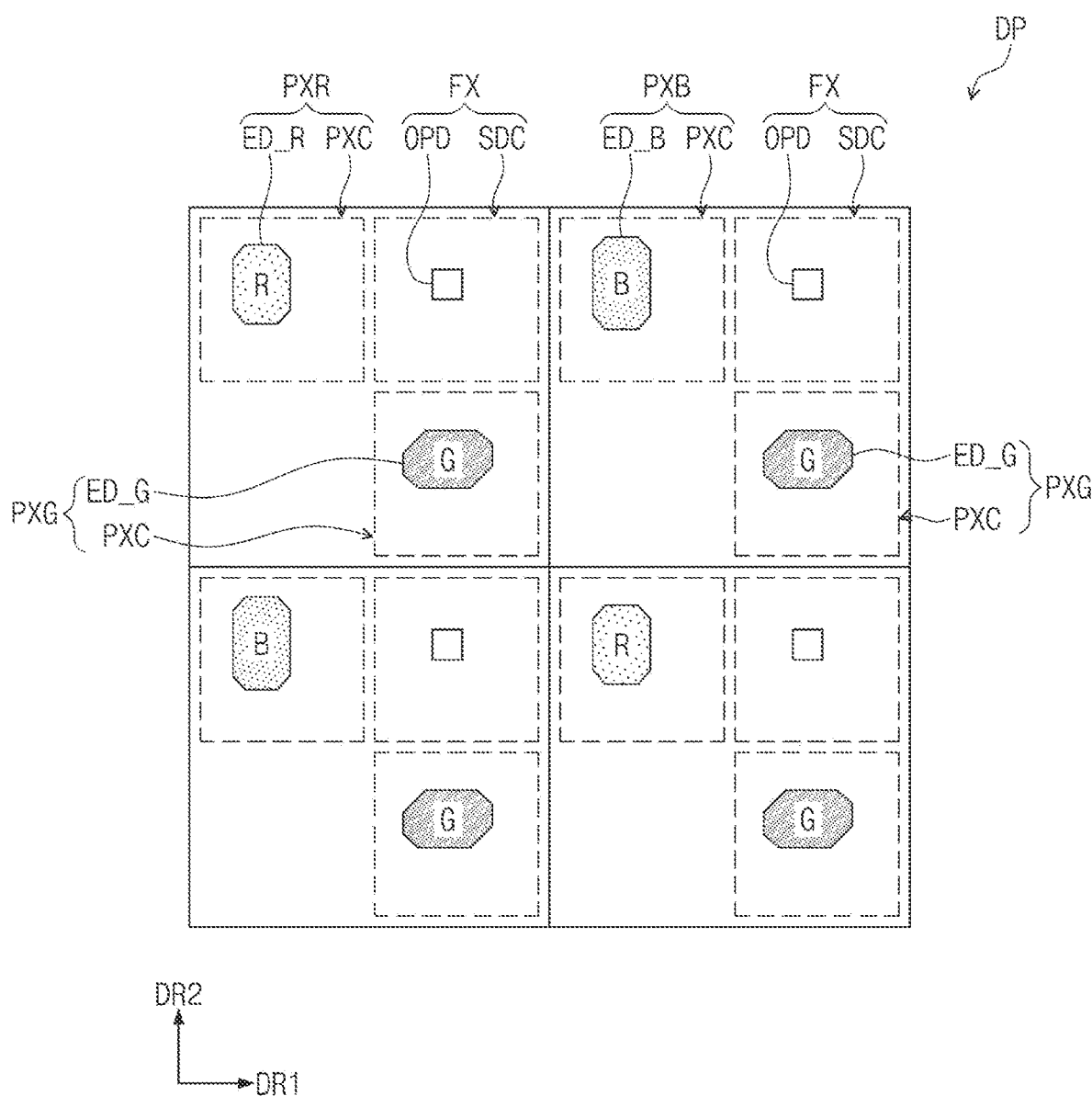
FIG. 4 is an enlarged plan view of a partial area of a display panel, according to an embodiment of the present disclosure.

FIG. 4 is an enlarged plan view of a partial area of a display panel, according to an embodiment of the present disclosure.

Referring to FIG. 4, pixels PXR, PXG, and PXB are arranged on the display panel DP. The pixel PXR includes a light emitting element ED_R and a pixel circuit PXC. The pixel PXG includes a light emitting element ED_G and a pixel circuit PXC. The pixel PXB includes a light emitting element ED_B and a pixel circuit PXC. Each of the pixels PX shown in FIG. 3 may correspond to one of the pixels PXR, PXG, and PXB shown in FIG. 4. Each of the sensors FX includes a light sensing element OPD and a sensor driving circuit SDC.

As shown in FIG. 4, the pixels PXR and PXB and the sensors FX are disposed in odd-numbered rows, or in other words, a first row and a third row. In an embodiment, in the first row and the third row, the pixels PXR and PXB and the sensors FX are alternately arranged along the first direction DR1. The pixels PXG (e.g., only the pixels PXG) are positioned in the second row (and in the fourth row).

In an embodiment, the pixel PXR may include a light emitting element ED_R that emits light of a first color (e.g., red). The pixel PXG may include a light emitting element ED_G that emits light of a second color (e.g., green). The pixel PXB includes a light emitting element ED_B that emits light of a third color (e.g., blue).

As shown in FIG. 4, the pixels PXR and PXB may be alternately and repeatedly positioned along the second direction DR2 as well as the first direction DR1. Each of the pixels PXG may be arranged between two light sensing elements OPD along the second direction DR2.

The arrangement structure of the pixels PX and the sensors FX is not limited to that illustrated in FIG. 4, and may be variously modified as needed or desired.

In an embodiment, the light emitting element ED_R may have a larger size than that of the light emitting element ED_G. Furthermore, the light emitting element ED_B may have a size larger than or equal to that of the light emitting element ED_R. The size of each of the light emitting elements ED_R, ED_G, and ED_B is not limited thereto, and may be variously modified and applied as needed or desired. For example, in an embodiment of the present disclosure, the light emitting elements ED_R, ED_G, and ED_B may have the same or substantially the same size as one another.

Further, the shape of each of the light emitting elements ED_R, ED_G, and ED_B may be variously modified as needed or desired, for example, such as into a polygon, a circle, an ellipse, and/or the like. In an embodiment, the shapes of the light emitting elements ED_R, ED_G, and ED_B may be different from one another. For example, the light emitting element ED_G may have a circular shape, and each of the light emitting elements ED_R and ED_B may have a quadrangle shape.

In an embodiment, an area size occupied by the sensor driving circuit SDC may be different from an area size occupied by the pixel circuit PXC.

Figure 5:
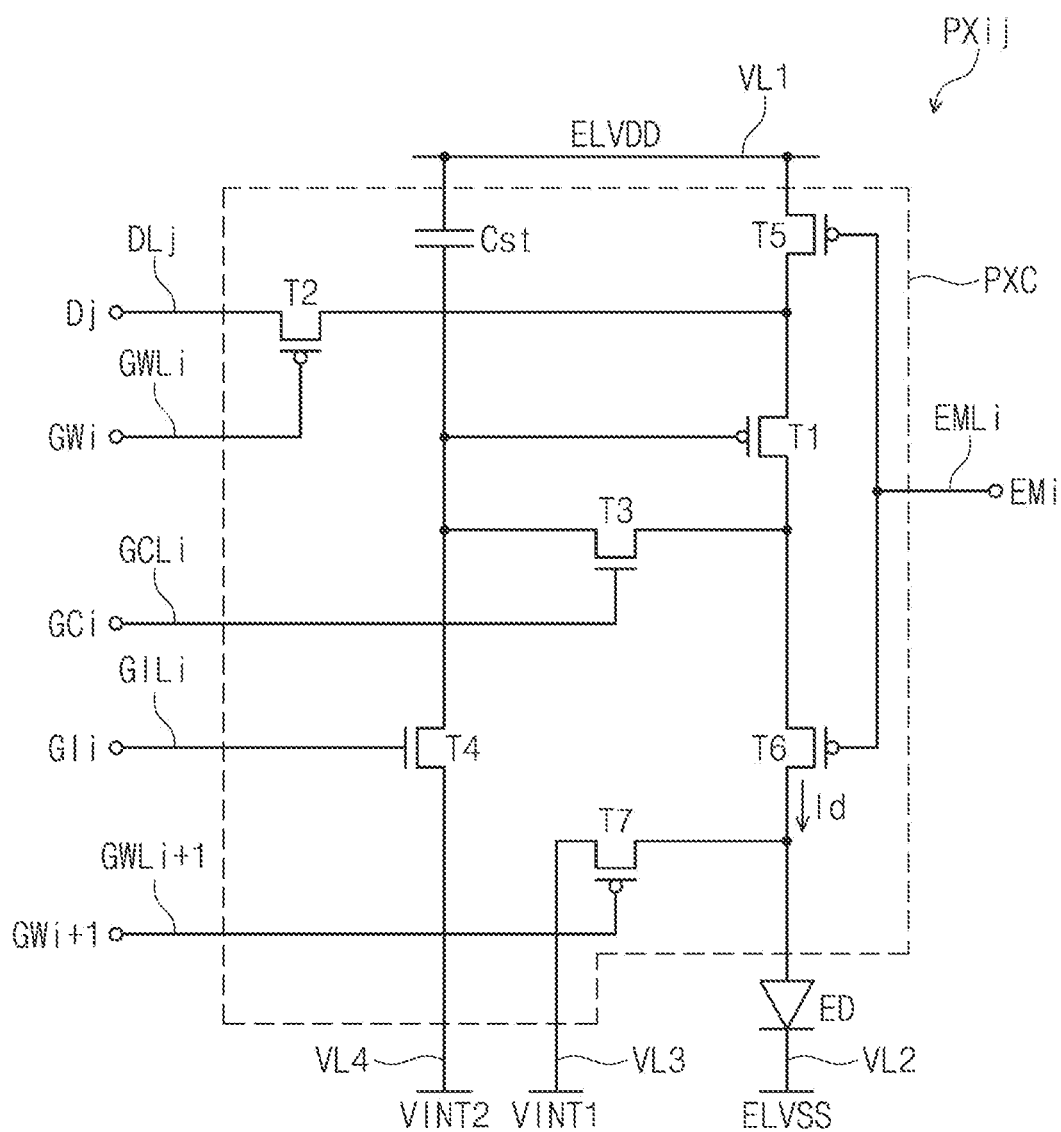
FIG. 5 is a circuit diagram of a pixel, according to an embodiment of the present disclosure.

FIG. 5 is a circuit diagram of a pixel, according to an embodiment of the present disclosure.

FIG. 5 illustrates one pixel PXij from among the pixels PX illustrated in FIG. 3. Each of the plurality of pixels PX shown in FIG. 3 may have the same or substantially the same circuit configuration as that of the pixel PXij shown in FIG. 5.

Referring to FIG. 5, the pixel PXij includes the pixel circuit PXC, and the at least one light emitting element ED. The light emitting element ED may be a light emitting diode. As an example, the light emitting element ED may be an organic light emitting diode including an organic light emitting layer. The pixel circuit PXC according to an embodiment includes first to seventh transistors T1, T2, T3, T4, T5, T6, and T7, and one capacitor Cst.

The third and fourth transistors T3 and T4 of the first to seventh transistors T1 to T7 may be N-type transistors that use an oxide semiconductor as a semiconductor layer. Each of the first, second, fifth, sixth, and seventh transistors T1, T2, T5, T6, and T7 may be a P-type transistor that has a low-temperature polycrystalline silicon (LTPS) semiconductor layer. However, the present disclosure is not limited thereto. In an embodiment, all of the first to seventh transistors T1 to T7 may be P-type transistors. In an embodiment, all of the first to seventh transistors T1 to T7 may be N-type transistors. In an embodiment, at least one of the first to seventh transistors T1 to T7 may be an N-type transistor, and the others thereof may be P-type transistors. A configuration of the pixel circuit PXC according to the present disclosure is not limited to the embodiment illustrated in FIG. 5. The pixel circuit PXC illustrated in FIG. 5 is only an example. For example, the configuration of the pixel circuit PXC may be variously modified and implemented as would be understood by those having ordinary skill in the art.

The pixel PXij is electrically connected to the scan lines GILi, GCLi, GWLi, and GWLi+1, the emission line EMLi, and the data line DLj. The scan lines GILi, GCLi, GWLi, and GWLi+1 may deliver scan signals GIi, GCi, GWi, and GWi+1, respectively. The emission line EMLi may deliver an emission signal EMi. The data line DLj delivers a data signal Dj. The data signal Dj may have a voltage level corresponding to the input image signal RGB that is input to the display device DD (e.g., see FIG. 3). First to fourth driving voltage lines VL1, VL2, VL3, and VL4 may deliver the first driving voltage ELVDD, the second driving voltage ELVSS, the first initialization voltage VINT1, and the second initialization voltage VINT2, respectively.

The first transistor T1 includes a first electrode connected with the first driving voltage line VL1 through the fifth transistor T5, a second electrode electrically connected with an anode of the light emitting element ED through the sixth transistor T6, and a gate electrode connected with one end of the capacitor Cst. The first transistor T1 may receive the data signal Dj delivered through the data line DLj depending on a switching operation of the second transistor T2, and then may supply a driving current Id to the light emitting element ED.

The second transistor T2 includes a first electrode connected to the data line DLj, a second electrode connected to the first electrode of the first transistor T1, and a gate electrode connected to the scan line GWLi. The second transistor T2 may be turned on in response to the scan signal GWi transferred through the scan line GWLi, and may transfer the data signal Dj transferred through the data line DLj to the first electrode of the first transistor T1.

The third transistor T3 includes a first electrode connected with the gate electrode of the first transistor T1, a second electrode connected with the second electrode of the first transistor T1, and a gate electrode connected with the scan line GCLi. The third transistor T3 may be turned on in response to the scan signal GCi transferred through the scan line GCLi, and thus, the gate electrode and the second electrode of the first transistor T1 may be connected to each other, or in other words, the first transistor T1 may be diode-connected.

The fourth transistor T4 includes a first electrode connected with the gate electrode of the first transistor T1, a second electrode connected with the fourth driving voltage line VL4 through which the second initialization voltage VINT2 is transferred, and a gate electrode connected with the scan line GILi. The fourth transistor T4 may be turned on in response to the scan signal GIi transferred through the scan line GILi, such that the second initialization voltage VINT2 is transferred to the gate electrode of the first transistor T1. As such, a voltage of the gate electrode of the first transistor T1 may be initialized. This operation may be referred to as an "an initialization operation".

The fifth transistor T5 includes a first electrode connected to the first driving voltage line VL1, a second electrode connected to the first electrode of the first transistor T1, and a gate electrode connected to the emission line EMLi.

The sixth transistor T6 includes a first electrode connected with the second electrode of the first transistor T1, a second electrode connected with the anode of the light emitting element ED, and a gate electrode connected to the emission line EMLi.

The fifth transistor T5 and the sixth transistor T6 may be concurrently or substantially simultaneously turned on in response to the emission control signal EMi transferred through the emission line EMLi. As such, the first driving voltage ELVDD may be compensated for through the diode-connected transistor T1, so as to be supplied to the light emitting element ED.

The seventh transistor T7 includes a first electrode connected to the anode of the light emitting element ED, a second electrode connected to the third driving voltage line VL3, and a gate electrode connected to the scan line GWLi+1. The seventh transistor T7 is turned on in response to the scan signal GWi+1 received through the scan line GWLi+1 to electrically connect the anode of the light emitting element ED and the third driving voltage line VL3 to each other.

One end of the capacitor Cst is connected to the gate electrode of the first transistor T1, and the other end of the capacitor Cst is connected to the first driving voltage line VL1. A cathode of the light emitting element ED may be connected with the second driving voltage line VL2 that transfers the second driving voltage ELVSS. However, the present disclosure is not limited to the structure of the pixel PXij illustrated in FIG. 5. For example, the number of transistors included in one pixel PXij, the number of capacitors included in the pixel PXij, and the connection relationships between the transistors and the capacitors may be variously modified as would be understood by those having ordinary skill in the art.

Figure 6:
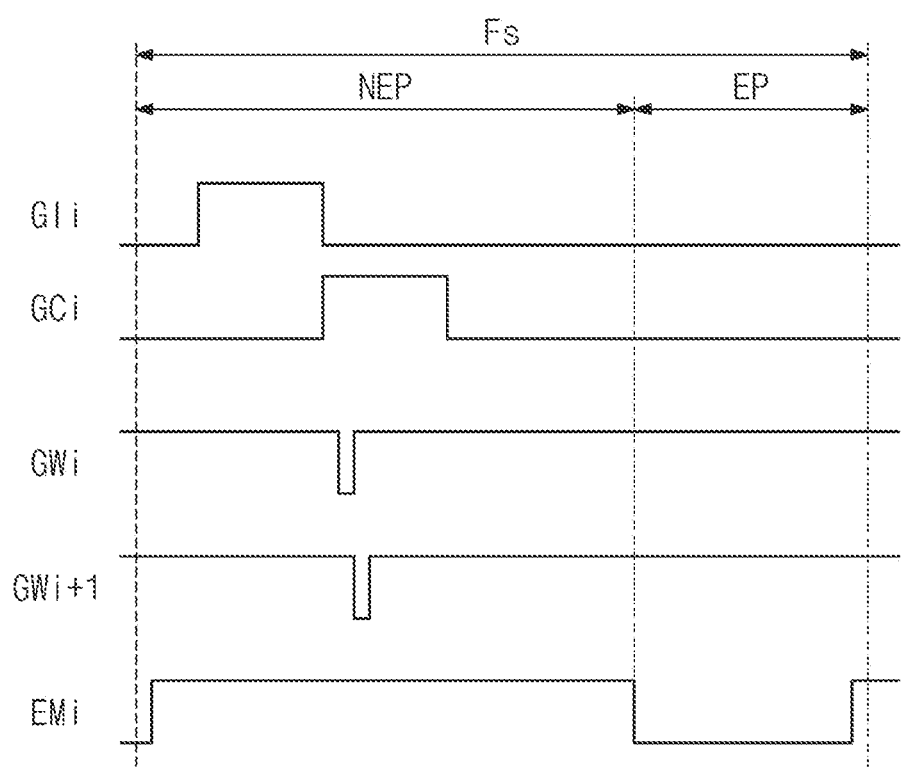
FIG. 6 is a timing diagram for an operation of the pixel illustrated in FIG. 5.

FIG. 6 is a timing diagram for an operation of the pixel illustrated in FIG. 5.

Referring to FIGS. 5 and 6, one frame Fs may include an emission period EP and a non-emission period NEP. The emission period EP may correspond to a low-level period (e.g., an active period) of the emission control signal EMi. The non-emission period NEP may correspond to a high-level period (e.g., an inactive period) of the emission control signal EMi.

The non-emission period NEP may include an initialization period and a data programming and compensation period.

When the scan signal GIi having a high level (e.g., an active level) is provided through the scan line GILi during the initialization period, the fourth transistor T4 is turned on. The second initialization voltage VINT2 is delivered to the gate electrode of the first transistor T1 through the fourth transistor T4, so as to initialize the first transistor T1.

Next, when the scan signal GCi having a high level (e.g., an active level) is supplied through the scan line GCLi during the data programming and compensation period, the third transistor T3 is turned on. The first transistor T1 is diode-connected by the third transistor T3, and thus, turned on to be forward-biased. At this time, when the scan signal GWi having a low level (e.g., an active level) is supplied through the scan line GWLi, the second transistor T2 is turned on. In this case, a compensation voltage, which is obtained by reducing the voltage of the data signal Dj supplied from the data line DLj by a threshold voltage of the first transistor T1, is applied to the gate electrode of the first transistor T1. In other words, a gate voltage applied to the gate electrode of the first transistor T1 may be a compensation voltage.

As the first driving voltage ELVDD and the compensation voltage are respectively applied to opposite ends of the capacitor Cst, charges corresponding to a difference between the first driving voltage ELVDD and the compensation voltage may be stored in the capacitor Cst.

In the meantime, the seventh transistor T7 is turned on in response to the scan signal GWi+1 having a low level (e.g., an active level) that is delivered through the scan line GWLi+1. As the seventh transistor T7 is turned on, the anode of the light emitting element ED is electrically connected to the third driving voltage line VL3. Accordingly, the anode of the light emitting element ED may be initialized to the first initialization voltage VINT1.

Next, during the emission period EP, the emission control signal EMi supplied from the emission line EMLi is changed from a high level to a low level. During the emission period EP, the fifth transistor T5 and the sixth transistor T6 are turned on by the emission control signal EMi having the low level. In this case, the driving current Id according to a voltage difference between the gate voltage of the gate electrode of the first transistor T1 and the first driving voltage ELVDD is generated and supplied to the light emitting element ED through the sixth transistor T6, and the driving current Id flows through the light emitting element ED. The light emitting element ED may emit light having a desired luminance corresponding to the driving current Id.

Figure 7:
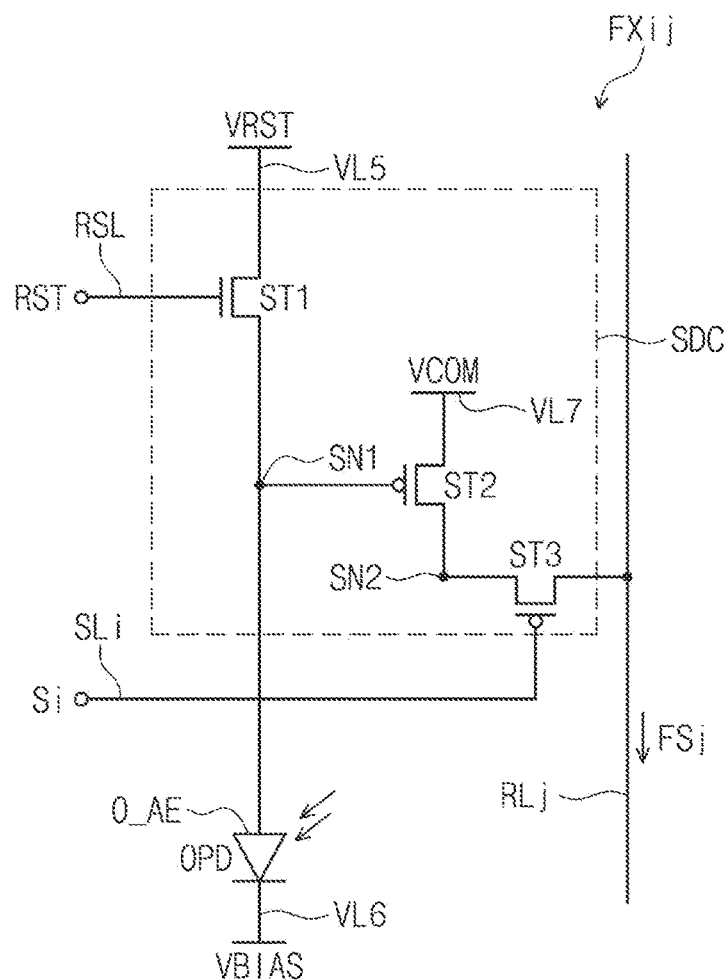
FIG. 7 is a circuit diagram of a sensor, according to an embodiment of the present disclosure.

FIG. 7 is a circuit diagram of a sensor, according to an embodiment of the present disclosure.

FIG. 7 shows one sensor FXij from among the plurality of sensors FX shown in FIG. 3. Each of the plurality of sensors FX shown in FIG. 3 may have the same or substantially the same circuit configuration as that of the sensor FXij illustrated in FIG. 7.

The sensor FXij is electrically connected to a sensor scan line SLi, a reset line RSL, and a readout line RLj.

The sensor FXij includes the light sensing element OPD and the sensor driving circuit SDC. The light sensing element OPD may be a photodiode. As an example, the light sensing element OPD may be an organic photodiode including an organic material as a photoelectric conversion layer. A light sensing anode O_AE of the light sensing element OPD may be connected with a first sensing node SN1, and a cathode thereof may be connected with a bias voltage line VL6 for transferring a bias voltage VBIAS. In an embodiment, the bias voltage VBIAS may be the same or substantially the same voltage as that of the second driving voltage ELVSS provided to the cathode of the light emitting element ED shown in FIG. 5.

The sensor driving circuit SDC includes three transistors ST1 to ST3. The three transistors ST1 to ST3 may include a reset transistor ST1, an amplification transistor ST2, and an output transistor ST3. At least one of the reset transistor ST1, the amplification transistor ST2, or the output transistor ST3 may be a P-type transistor, and the other(s) thereof may be an N-type transistor. In an embodiment, the reset transistor ST1 may be the same kind of N-type transistor as that of the third transistor T3 of the pixel PXij shown in FIG. 5, and each of the amplification transistor ST2 and the output transistor ST3 may be the same kind of P-type transistor as that of the first and second transistors T1 and T2 of the pixel PXij shown in FIG. 5. However, the present disclosure is not limited thereto. In an embodiment, all of the reset transistor ST1, the amplification transistor ST2, and the output transistor ST3 may be P-type transistors. In an embodiment, all of the reset transistor ST1, the amplification transistor ST2, and the output transistor ST3 may be N-type transistors.

The reset transistor ST1 includes a first electrode connected with a reset voltage line VL5 that receives the reset voltage VRST, a second electrode connected with the first sensing node SN1, and a gate electrode connected with the reset line RSL that receives the reset signal RST. The reset transistor ST1 may reset a potential of the first sensing node SN1 to the reset voltage VRST in response to the reset signal RST. In an embodiment, the reset voltage VRST may have a voltage level lower than that of the bias voltage VBIAS.

The amplification transistor ST2 includes a first electrode connected with a sensor driving voltage line VL7 for receiving a sensor driving voltage VCOM, a second electrode connected with a second sensing node SN2, and a gate electrode connected with the first sensing node SN1. In an embodiment, the sensor driving voltage VCOM may have the same or substantially the same voltage level as that of one of the first driving voltage ELVDD, the first initialization voltage VINT1, or the second initialization voltage VINT2 that are provided to the pixel PXij as shown in FIG. 5. The amplification transistor ST2 may provide a current corresponding to a potential of the first sensing node SN1 to the second sensing node SN2.

The output transistor ST3 includes a first electrode connected with the second sensing node SN2, a second electrode connected with the readout line RLj, and a gate electrode connected with the sensor scan line SLi for receiving the sensor scan signal Si. The output transistor ST3 may output a sensing signal FSj to the readout line RLj in response to the sensor scan signal Si.

The circuit configuration of the sensor driving circuit SDC according the present disclosure is not limited to that illustrated in FIG. 7. The sensor driving circuit SDC illustrated in FIG. 7 is only an example, and the configuration of the sensor driving circuit SDC may be variously modified and implemented as would be understood by those having ordinary skill in the art.

Figure 8:
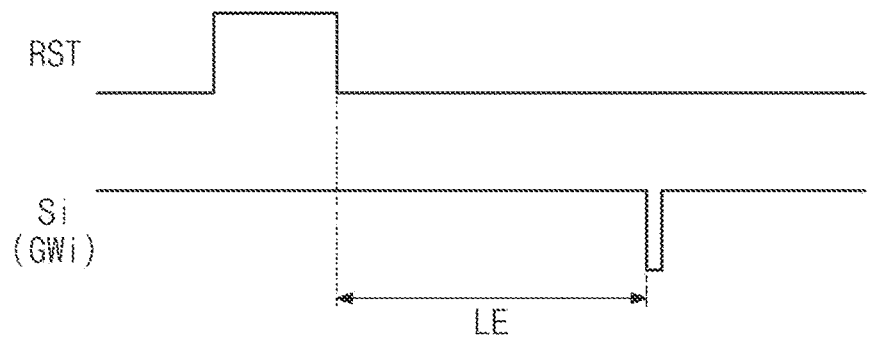
FIG. 8 is a timing diagram for an operation of the sensor illustrated in FIG. 7.

FIG. 8 is a timing diagram for an operation of the sensor FXij illustrated in FIG. 7.

Referring to FIGS. 7 and 8, when the reset signal RST transitions to a high level (e.g., an active level), the reset transistor ST1 turns on. As the reset transistor ST1 is turned on, the first sensing node SN1 may be initialized to the reset voltage VRST.

After the reset signal RST transitions to a low level (e.g., an inactive level), the sensor FXij is exposed to light during a light exposure period LE. When a user's hand touches a display surface, the light sensing element OPD may generate photocharges corresponding to light reflected by the user's hand, and the generated photocharges may be accumulated in the first sensing node SN1.

The amplification transistor ST2 may be a source follower amplifier that generates a source-drain current in proportion to a charge amount of the first sensing node SN1 input to the gate electrode of the amplification transistor ST2.

While the sensor scan signal Si is at an inactive level (e.g., a high level), the output transistor ST3 is turned off. When the sensor scan signal Si transitions to an active level (e.g., a low level), the output transistor ST3 is turned on. When the output transistor ST3 is turned on, a sensing signal FSj corresponding to a current flowing through the amplification transistor ST2 may be output to the readout line RLj.

In an embodiment, the sensor scan signal Si may be the same signal as the scan signal GWi shown in FIGS. 5 and 6. In other words, the pixels PXij and the sensors FXij arranged in the i-th row may receive the same scan signal GWi.

In an embodiment, during a fingerprint sensing mode, the light sensing element OPD may generate photocharges corresponding to light reflected by a ridge of a fingerprint and/or a valley between ridges of the fingerprint. During the fingerprint sensing mode, the sensing signal FSj output from the sensor FXij may be a signal corresponding to the user's fingerprint.

In an embodiment, during a blood pressure measurement mode, the light sensing element OPD may generate photocharges corresponding to light reflected from blood vessels located under a dermal layer of the user's skin. During cardiac systole, blood moves to the periphery, increasing arterial blood volume. On the other hand, during cardiac diastole, blood volume decreases. This change in blood volume changes the reflected light. During the blood pressure measurement mode, the sensing signal FSj output from the sensor FXij may be a signal corresponding to the user's blood pressure.

In an embodiment, during a touch sensing mode, the light sensing element OPD may generate photocharges corresponding to light reflected by the user's touch. The sensing signal FSj output from the sensor FXij during the touch sensing mode may be a signal indicating whether or not a user performs a touch operation.

Figure 9:
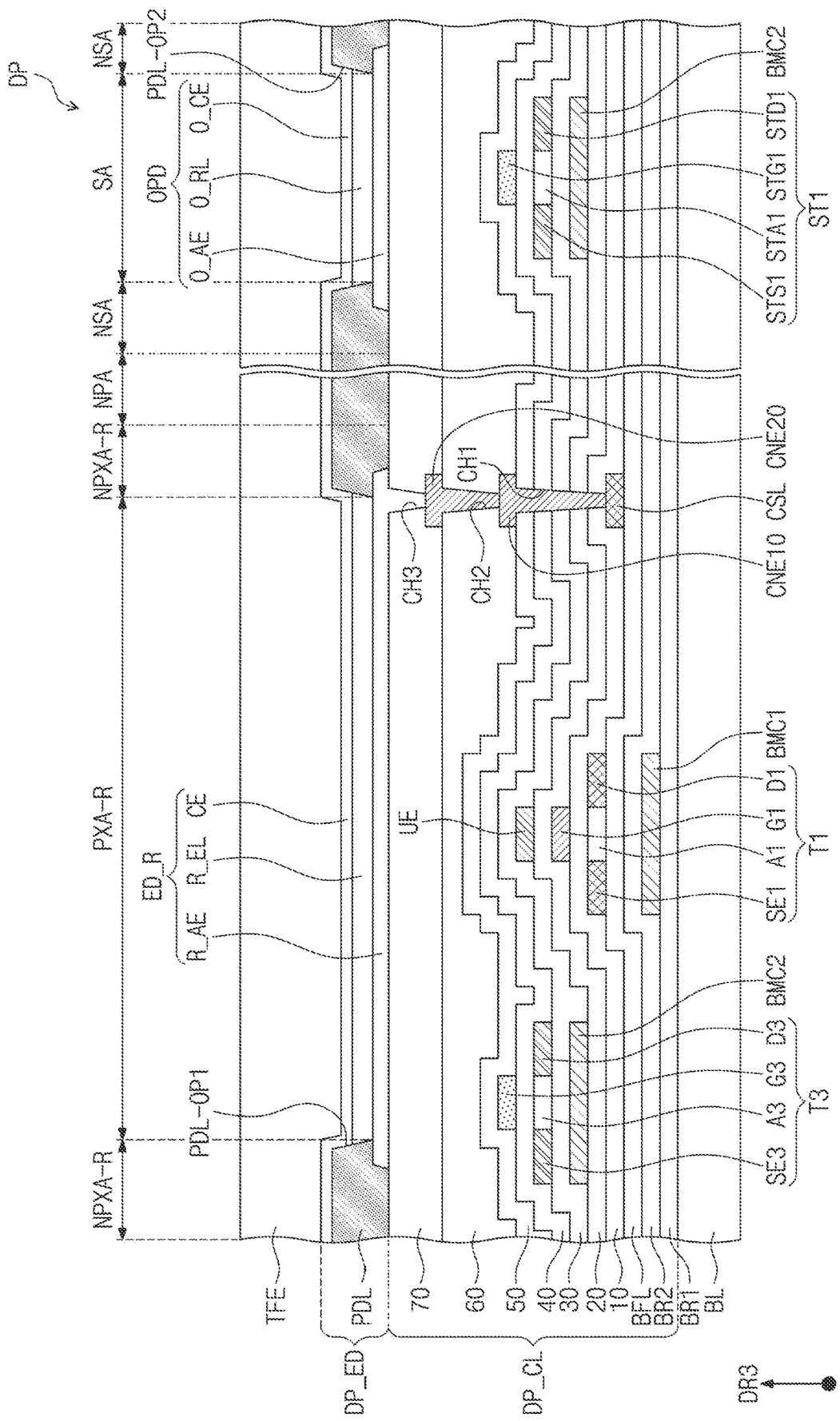
FIG. 9 is a cross-sectional view of a display panel, according to an embodiment of the present disclosure.

FIG. 9 is a cross-sectional view of the display panel DP, according to an embodiment of the present disclosure. FIG. 9 shows portions of the first and third transistors T1 and T3 shown in FIG. 5, and a portion of the reset transistor ST1 shown in FIG. 7.

Referring to FIG. 9, the display panel DP may include a base layer BL, a circuit layer DP_CL disposed on the base layer BL, an element layer DP_ED, and an encapsulation layer TFE.

The base layer BL may include a synthetic resin layer. The synthetic resin layer may include a thermosetting resin. In more detail, the synthetic resin layer may be a polyimide-based resin layer, but the material thereof is not particularly limited thereto. The synthetic resin layer may include at least one of an acrylate-based resin, a methacrylate-based resin, polyisoprene, a vinyl-based resin, an epoxy-based resin, a urethane-based resin, a cellulose-based resin, a siloxane-based resin, a polyamide-based resin, or a perylene-based resin. The base layer may include a glass substrate, a metal substrate, an organic/inorganic composite substrate, or the like.

At least one inorganic layer is formed on an upper surface of the base layer BL. The inorganic layer may include at least one of aluminum oxide, titanium oxide, silicon oxide, silicon oxynitride, zirconium oxide, or hafnium oxide. The inorganic layer may be formed of multiple layers. The multi-layered inorganic layers may constitute barrier layers BR1 and BR2, and/or a buffer layer BFL, which will be described in more detail below. The barrier layers BR1 and BR2 and the buffer layer BFL may be disposed selectively.

The barrier layers BR1 and BR2 prevent or substantially prevent foreign objects from being introduced from the outside. The barrier layers BR1 and BR2 may include a silicon oxide layer and a silicon nitride layer. Each of the silicon oxide layer and the silicon nitride layer may include a plurality of layers, and the silicon oxide layers and the silicon nitride layers may be alternately stacked.

The barrier layers BR1 and BR2 may include the first barrier layer BR1 and the second barrier layer BR2. A first back metal layer BMC1 may be interposed between the first barrier layer BR1 and the second barrier layer BR2. In an embodiment of the present disclosure, the first back metal layer BMC1 may be omitted as needed or desired.

The buffer layer BFL may be disposed on the barrier layers BR1 and BR2. The buffer layer BFL improves a bonding force between the base layer BL and a semiconductor pattern and/or a conductive pattern. The buffer layer BFL may include a silicon oxide layer and a silicon nitride layer. The silicon oxide layer and the silicon nitride layer may be alternately stacked.

A first semiconductor pattern may be disposed on the buffer layer BFL. The first semiconductor pattern may include a silicon semiconductor. For example, the silicon semiconductor may include amorphous silicon or polycrystalline silicon. For example, the first semiconductor pattern may include low-temperature polysilicon.

FIG. 9 illustrates only a portion of the first semiconductor pattern disposed on the buffer layer BFL. Another portion of the first semiconductor pattern may be further disposed in another area. The first semiconductor pattern may be arranged across the pixels in a suitable rule (e.g., a specific or predetermined rule). The first semiconductor pattern may have different electrical characteristics depending on whether or not the first semiconductor pattern is doped. The first semiconductor pattern may include a first area having high conductivity, and a second area having low conductivity. The first area may be doped with an N-type dopant or a P-type dopant. A P-type transistor may include an area doped with the P-type dopant, and an N-type transistor may include an area doped with the N-type dopant. The second area may be an undoped area, or an area doped with a concentration lower than a concentration of the first area.

The conductivity of the first area is greater than the conductivity of the second area. The first area may serve or substantially serve as an electrode or a signal line. The second area may correspond to or substantially correspond to an active area (or a channel) of a transistor. In other words, a part of the semiconductor pattern may be an active area of the transistor. Another part thereof may be a source or drain of the transistor. Another part thereof may be a connection electrode or a connection signal line.

A first electrode SE1, a channel part A1, and a second electrode D1 of the first transistor T1 are formed from the first semiconductor pattern. The first electrode SE1 and the second electrode D1 of the first transistor T1 extend in opposite directions from the channel part A1.

A portion of a connection signal line CSL formed from the first semiconductor pattern is illustrated in FIG. 9. The connection signal line CSL may be electrically connected to the second electrode of the sixth transistor T6 (e.g., see FIG. 5) on a plane (e.g., in a plan view).

A first insulating layer 10 may be disposed on the buffer layer BFL. The first insulating layer 10 may overlap with a plurality of pixels in common, and may cover the first semiconductor pattern. The first insulating layer 10 may be an inorganic layer and/or an organic layer, and may have a single layer or multi-layered structure. The first insulating layer 10 may include at least one of aluminum oxide, titanium oxide, silicon oxide, silicon nitride, silicon oxynitride, zirconium oxide, or hafnium oxide. In an embodiment, the first insulating layer 10 may be a single silicon oxide layer. An insulating layer of the circuit layer DP_CL, which is described in more detail below, as well as the first insulating layer 10 may be an inorganic layer and/or an organic layer, and may have a single layer structure or a multi-layered structure. The inorganic layer may include at least one of the above-described materials, but is not limited thereto.

A third electrode G1 of the first transistor T1 is disposed on the first insulating layer 10. The third electrode G1 may be a portion of a metal pattern. The third electrode G1 of the first transistor T1 overlaps with the channel part A1 of the first transistor T1. In a process of doping the first semiconductor pattern, the third electrode G1 of the first transistor T1 may function as a mask. The third electrode G1 may include, but is not limited to, titanium (Ti), silver (Ag), an alloy containing silver (Ag), molybdenum (Mo), an alloy containing molybdenum (Mo), aluminum (Al), an alloy containing aluminum (Al), an aluminum nitride (AlN), tungsten (W), a tungsten nitride (WN), copper (Cu), indium tin oxide (ITO), indium zinc oxide (IZO), or the like.

A second insulating layer 20 may be disposed on the first insulating layer 10, and may cover the third electrode G1 of the first transistor T1. The second insulating layer 20 may be an inorganic layer and/or an organic layer, and may have a single layer structure or a multi-layered structure. The second insulating layer 20 may include at least one of silicon oxide, silicon nitride, or silicon oxynitride. In an embodiment, the second insulating layer 20 may have a multi-layered structure including a silicon oxide layer and a silicon nitride layer.

An upper electrode UE and a second back metal layer BMC2 may be disposed on the second insulating layer 20. The upper electrode UE may overlap with the third electrode G1. The upper electrode UE may be a portion of a metal pattern. A portion of the third electrode G1 and the upper electrode UE overlapping with the portion of the third electrode G1 may define the capacitor Cst (e.g., see FIG. 5). In an embodiment of the present disclosure, the second insulating layer 20 may be replaced with an insulating pattern. In this case, the upper electrode UE may be disposed on the insulating pattern, and the upper electrode UE may serve as a mask for forming the insulating pattern from the second insulating layer 20.

The second back metal layer BMC2 may be disposed to correspond to a lower portion of an oxide thin film transistor (e.g., the third transistor T3). The second back metal layer BMC2 may receive a constant or substantially constant voltage or a signal.

A third insulating layer 30 may be disposed on the second insulating layer 20, and may cover the upper electrode UE and the second back metal layer BMC2. The third insulating layer 30 may have a single layer or multi-layered structure. For example, the third insulating layer 30 may have a multi-layered structure including a silicon oxide layer and a silicon nitride layer.

A second semiconductor pattern may be disposed on the third insulating layer 30. The second semiconductor pattern may include an oxide semiconductor. The oxide semiconductor may include a plurality of areas that are distinguished from one another depending on whether or not a metal oxide is reduced. An area (hereinafter referred to as a "reduction area") in which the metal oxide is reduced has a higher conductivity than that of an area (hereinafter referred to as a "non-reduction area") in which the metal oxide is not reduced. The reduction area serves or substantially serves as a source/drain area of a transistor or a signal line. The non-reduction area corresponds to or substantially corresponds to an active area (alternatively, a semiconductor area or a channel) of the transistor. In other words, a part of the second semiconductor pattern may be the active area of the transistor, another part thereof may be the source/drain area of the transistor, and another part thereof may be a signal transmission area.

A first electrode SE3, a channel part A3, and a second electrode D3 of the third transistor T3 are formed from the second semiconductor pattern. The first electrode SE3 and the second electrode D3 include a metal reduced from a metal oxide semiconductor. The first electrode SE3 and the second electrode D3 may extend in directions opposite to each other from the channel part A3 on a cross section (e.g., in a cross-sectional view).

A fourth insulating layer 40 may be disposed on the third insulating layer 30. The fourth insulating layer 40 may overlap with a plurality of pixels in common, and may cover the second semiconductor pattern. The fourth insulating layer 40 may include at least one of aluminum oxide, titanium oxide, silicon oxide, silicon nitride, silicon oxynitride, zirconium oxide, or hafnium oxide.

A third electrode G3 of the third transistor T3 is disposed on the fourth insulating layer 40. The third electrode G3 may be a portion of a metal pattern. The third electrode G3 of the third transistor T3 overlaps with the channel part A3 of the third transistor T3. The third electrode G3 may function as a mask in a process of doping the second semiconductor pattern. In an embodiment of the present disclosure, the fourth insulating layer 40 may be replaced with an insulating pattern.

A fifth insulating layer 50 may be disposed on the fourth insulating layer 40, and may cover the third electrode G3. The fifth insulating layer 50 may be an inorganic layer.

A first connection electrode CNE10 may be disposed on the fifth insulating layer 50. The first connection electrode CNE10 may be connected to the connection signal line CSL through a first contact hole CH1 penetrating the first to fifth insulating layers 10, 20, 30, 40, and 50.

The sixth insulating layer 60 may be disposed on the fifth insulating layer 50. The sixth insulating layer 60 may be an organic layer. The organic layer may include one or more general purpose polymers, such as benzocyclobutene (BCB), polyimide, hexamethyldisiloxane (HMDSO), polymethylmethacrylate (PMMA), or polystyrene (PS), a polymer derivative having a phenolic group, an acrylic polymer, an imide-based polymer, an aryl ether-based polymer, an amide-based polymer, a fluorine-based polymer, a p-xylene-based polymer, a vinyl alcohol-based polymer, and/or a suitable blend thereof, but is not particularly limited thereto.

A second connection electrode CNE20 may be disposed on the sixth insulating layer 60. The second connection electrode CNE20 may be connected to the first connection electrode CNE10 through a second contact hole CH2 penetrating the sixth insulating layer 60. The seventh insulating layer 70 may be disposed on the sixth insulating layer 60, and may cover the second connection electrode CNE20. The seventh insulating layer 70 may be an organic layer.

A first electrode layer is disposed on the circuit layer DP_CL. A pixel defining layer PDL is formed on the first electrode layer. The first electrode layer may include a first anode R_AE and the light sensing anode O_AE. In an embodiment, the first anode R_AE and the light sensing anode O_AE are disposed on the seventh insulating layer 70. The first anode R_AE may be connected to the second connection electrode CNE20 through a third contact hole CH3 penetrating the seventh insulating layer 70. FIG. 9 shows only the first anode R_AE corresponding to red light. However, the first electrode layer may further include a second anode corresponding to green light and a third anode corresponding to blue light.

First and second film openings PDL-OP1 and PDL-OP2 are provided at (e.g., in or on) the pixel defining layer PDL. The first film opening PDL-OP1 exposes at least a part of the first anode R_AE. The second film opening PDL-OP2 exposes at least a part of the light sensing anode O_AE.

In an embodiment of the present disclosure, the pixel defining layer PDL may further include a black material. The pixel defining layer PDL may include a black organic dye/pigment, such as carbon black, aniline black, or the like. The pixel defining layer PDL may be formed by mixing a blue organic material and a black organic material with each other. The pixel defining layer PDL may further include a liquid-repellent organic material.

As shown in FIG. 9, the display panel DP may include an emission area PXA-R, and a non-emission area NPXA-R adjacent to the emission area PXA-R. The non-emission area NPXA-R may surround (e.g., around a periphery of) the emission area PXA-R. In an embodiment, the emission area PXA-R is defined to correspond to a partial area of the first anode R_AE that is exposed by the first film opening PDL-OP1.

A light emitting layer may be disposed on the first electrode layer. The light emitting layer may include red, green and blue light emitting layers. The red, green, and blue light emitting layers may be disposed in areas corresponding to the first film openings PDL-OP1. The red, green, and blue light emitting layers may be separately formed in the red, green, and blue pixels PXR, PXG, and PXB illustrated in FIG. 4, respectively. Each of the red, green, and blue light emitting layers may include an organic material and/or an inorganic material. The red, green, and blue light emitting layers may generate a suitable colored light (e.g., a predetermined colored light). For example, the light emitting layer R_EL may generate red light. FIG. 9 shows that the light emitting layer R_EL is disposed in an area corresponding to the first film opening PDL-OP1.

In an embodiment, patterned red, green, and blue light emitting layers are described. However, one light emitting layer may be commonly disposed in a plurality of emission areas. In this case, the light emitting layer may generate white light or blue light. Also, the light emitting layer may have a multi-layered structure referred to as a "tandem" structure.

The light emitting layer R_EL may include a low-molecular organic material or a high-molecular organic material as a light emitting material. A cathode CE is disposed on the light emitting layer R_EL. As an example, the cathode CE may be commonly disposed in the emission area PXA-R, the non-emission area NPXA-R, and a non-pixel area NPA.

The circuit layer DP_CL may further include the sensor driving circuit SDC (e.g., see FIG. 7). For convenience of illustration, the reset transistor ST1 of the sensor driving circuit SDC is shown in FIG. 9. A first electrode STS1, a channel part STA1, and a second electrode STD1 of the reset transistor ST1 are formed from the second semiconductor pattern. The first electrode STS1 and the second electrode STD1 include a metal reduced from a metal oxide semiconductor. The fourth insulating layer 40 is disposed to cover the first electrode STS1, the channel part STA1, and the second electrode STD1 of the reset transistor ST1. A third electrode (e.g., the gate electrode) STG1 of the reset transistor ST1 is disposed on the fourth insulating layer 40. In an embodiment, the third electrode STG1 may be a part of the metal pattern. The third electrode STG1 of the reset transistor ST1 overlaps with the channel part STA1 of the reset transistor ST1.

In an embodiment of the present disclosure, the reset transistor ST1 may be disposed at (e.g., in or on) the same layer as that of the third transistor T3. In other words, the first electrode STS1, the channel part STA1, and the second electrode STD1 of the reset transistor ST1 may be formed through a process that is the same or substantially the same as that of the first electrode SE3, the channel part A3, and the second electrode D3 of the third transistor T3. The third electrode STG1 of the reset transistor ST1 may be concurrently or substantially simultaneously formed through the same or substantially the same process as that of the third electrode G3 of the third transistor T3. The first electrode and the second electrode of each of the amplification transistor ST2 and the output transistor ST3 of the sensor driving circuit SDC may be formed through the same or substantially the same process as that of the first electrode SE1 and the second electrode D1 of the first transistor T1. The reset transistor ST1 and the third transistor T3 may be formed at (e.g., in or on) the same layer as each other through the same or substantially the same process. Accordingly, because an additional process for forming the reset transistor ST1 is not used, process efficiency and costs may be reduced.

The element layer DP_ED may further include the light sensing element OPD (e.g., see FIG. 7). FIG. 9 shows only one light sensing element OPD.

The light sensing element OPD may include the light sensing anode O_AE, a photoelectric conversion layer O_RL, and a cathode O_CE. The light sensing anode O_AE may be disposed at (e.g., in or on) the same layer as that of the first electrode layer. In other words, the light sensing anode O_AE may be disposed on the circuit layer DP_CL, and may be concurrently or substantially simultaneously formed through the same or substantially the same process as that of the first anode R_AE.

The second film opening PDL-OP2 of the pixel defining layer PDL exposes at least part of the light sensing anode O_AE. The photoelectric conversion layer O_RL is disposed on the light sensing anode O_AE exposed by the second film opening PDL-OP2. The photoelectric conversion layer O_RL may include an organic photo-sensing material. The photoelectric cathode O_CE may be disposed on the photoelectric conversion layer O_RL. The photoelectric cathode O_CE may be concurrently or substantially simultaneously formed through the same or substantially the same process as that of the cathode CE. As an example, the photoelectric cathode O_CE may be integrated with the cathode CE together.

Each of the light sensing anode O_AE and the photoelectric cathode O_CE may receive an electrical signal. The photoelectric cathode O_CE may receive a signal different from that of the light sensing anode O_AE. Accordingly, an electric field (e.g., a predetermined electric field) may be formed between the light sensing anode O_AE and the photoelectric cathode O_CE. The photoelectric conversion layer O_RL generates an electrical signal corresponding to the light incident on a sensor. The photoelectric conversion layer O_RL may generate charges by absorbing the energy of the incident light. For example, the photoelectric conversion layer O_RL may include a light-sensitive semiconductor material.

The charges generated by the photoelectric conversion layer O_RL may change the electric field between the light sensing anode O_AE and the photoelectric cathode O_CE. The amount of charge generated by the photoelectric conversion layer O_RL may vary depending on whether or not light is incident onto the light sensing element OPD, the amount of light incident onto the light sensing element OPD, and the intensity of light incident onto the light sensing element OPD. Accordingly, the electric field formed between the light sensing anode O_AE and the photoelectric cathode O_CE may be changed. The light sensing element OPD according to an embodiment of the present disclosure may obtain one of the fingerprint, the blood pressure, or the touch information of a user through a change in the electric field between the light sensing anode O_AE and the photoelectric cathode O_CE.

However, the present disclosure is not limited thereto. The light sensing element OPD may include a phototransistor that uses the photoelectric conversion layer O_RL as an active layer. In this case, the light sensing element OPD may obtain fingerprint information by sensing the amount of current flowing through the phototransistor. The light sensing element OPD according to an embodiment of the present disclosure may include various suitable photoelectric conversion elements capable of generating electrical signals in response to a change in the amount of light, but the present disclosure is not limited to any particular embodiment.

The encapsulation layer TFE is disposed on the element layer DP_ED. The encapsulation layer TFE includes at least one inorganic layer and/or at least one organic layer. In an embodiment of the present disclosure, the encapsulation layer TFE may include two inorganic layers and an organic layer disposed therebetween. In an embodiment of the present disclosure, a thin film encapsulation layer may include a plurality of inorganic layers and a plurality of organic layers, which are alternately stacked.

The encapsulation inorganic layer protects the light emitting element ED_R and the light sensing element OPD from moisture/oxygen, and the encapsulation organic layer protects the light emitting element ED_R and the light sensing element OPD from foreign substances. The encapsulation inorganic layer may include a silicon nitride layer, a silicon oxynitride layer, a silicon oxide layer, a titanium oxide layer, an aluminum oxide layer, or the like, but is not specifically limited thereto. The encapsulation organic layer may include an acryl-based organic layer, but is not specifically limited thereto.

Figure 10:
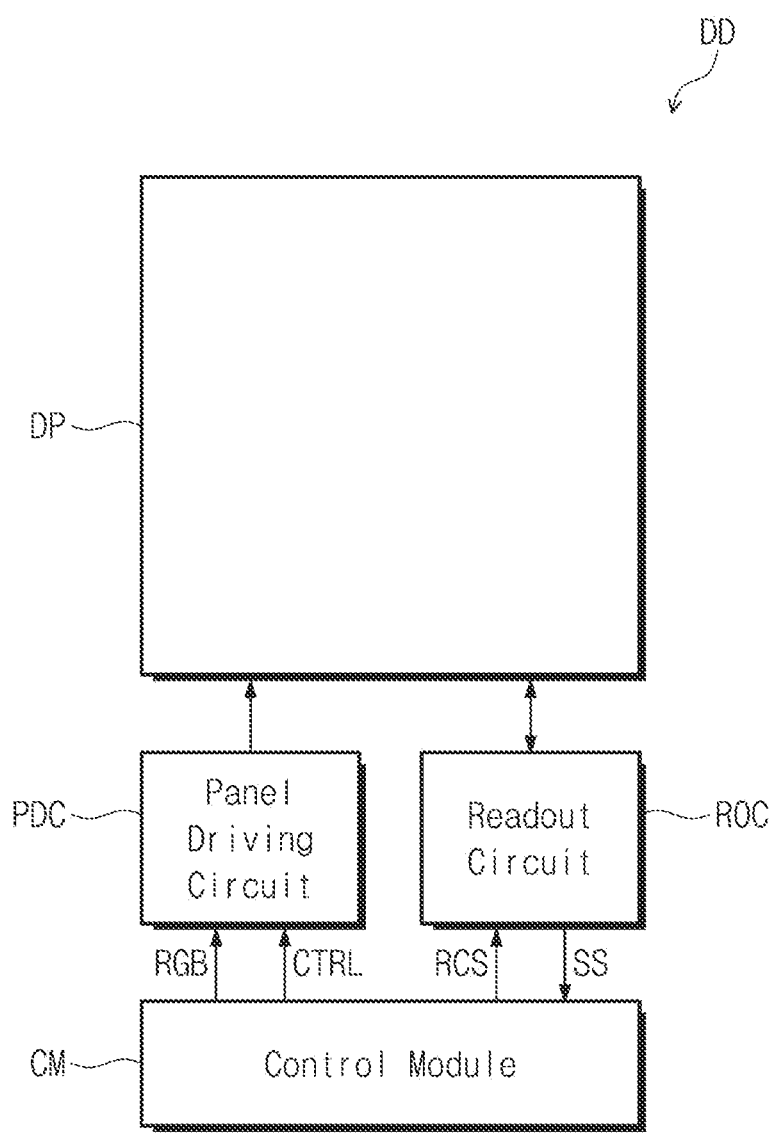
FIG. 10 is a block diagram of a display device, according to an embodiment of the present disclosure.

FIG. 10 is a block diagram of a display device, according to an embodiment of the present disclosure.

The display device DD may include the display panel DP, the panel driving circuit PDC, the readout circuit ROC, and a control module (e.g., a controller or a control circuit) CM. The panel driving circuit PDC may include the driving controller 100, the data driver 200, the scan and sensor driver 300, the light emitting driver 400, and the voltage generator 500, which are described above with reference to FIG. 3.

The control module CM may allow the panel driving circuit PDC to display an image on the display panel DP. The control module CM provides the input image signal RGB and the control signal CTRL to the panel driving circuit PDC.

The control module CM may control the readout circuit ROC, such that the display panel DP operates in a blood pressure sensing mode (e.g., a first mode), a fingerprint sensing mode (e.g., a second mode), and a touch sensing mode (e.g., a third mode). The control module CM may provide the readout control signal RCS to the readout circuit ROC, and may receive the readout signal SS from the readout circuit ROC.

Figure 11:
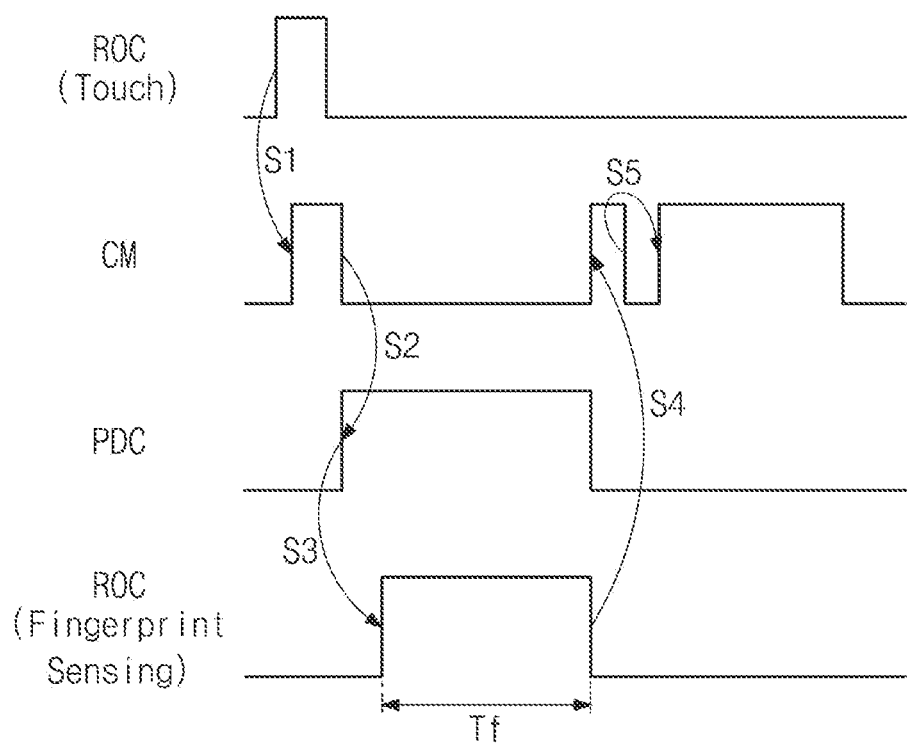
FIG. 11 is a diagram for an operation in a fingerprint sensing mode of a control module of a display device, according to an embodiment of the present disclosure.

FIG. 11 is a diagram for an operation in a fingerprint sensing mode of the control module CM of the display device DD, according to an embodiment of the present disclosure.

Figure 12:
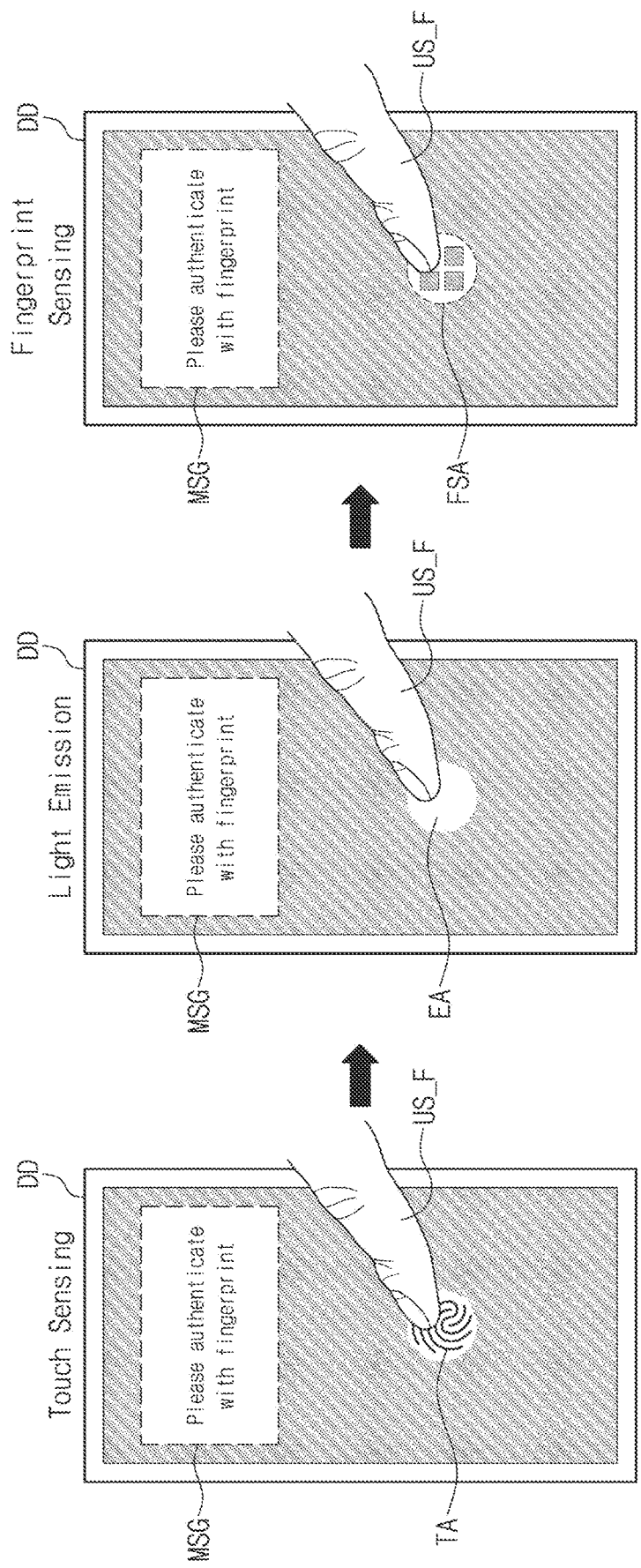
FIG. 12 is a diagram showing an image displayed on a display device in a fingerprint sensing mode.

FIG. 12 is a diagram showing an image displayed on the display device DD in a fingerprint sensing mode.

Referring to FIGS. 10, 11, and 12, the display device DD may operate in a touch sensing process, a light emitting process, and a fingerprint sensing process in the fingerprint sensing mode. In the touch sensing process, when a special message MSG saying "please authenticate with fingerprint" is displayed at a suitable location (e.g., a predetermined location) on the display device DD, a user may touch the user's finger US_F to a touch area TA of the display device DD. The kind and form of the message MSG displayed on the display device DD may be variously modified as needed or desired. Also, a touch sensing process may be performed without the special message MSG. For example, even while not displaying an image to save power, the display device DD may detect a touch of the user's finger US_F, and may perform user authentication and an unlocking function.

When the touch by the user's finger US_F is detected by the readout circuit ROC, the control module CM of the display device DD receives the readout signal SS from the readout circuit ROC (S1). In the light emitting process, the control module CM outputs, to the panel driving circuit PDC, the input image signal RGB and the control signal CTRL, which are used to control the luminance of an emission area EA of the display panel DP, in response to the readout signal SS from the readout circuit ROC (S2).

In the fingerprint sensing process, the control module CM outputs the readout control signal RCS for selecting a fingerprint sensing area FSA of the display panel DP to the readout circuit ROC (S3). The readout circuit ROC performs control for sensing a fingerprint from the fingerprint sensing area FSA of the display panel DP in response to the readout control signal RCS from the control module CM.

In an embodiment, during a fingerprint sensing time Tf, the readout circuit ROC may sense a fingerprint from the fingerprint sensing area FSA of the display panel DP. The readout circuit ROC provides the control module CM with the readout signal SS corresponding to a signal received from the fingerprint sensing area FSA of the display panel DP (S4).

The control module CM performs an authentication process by comparing the readout signal SS from the readout circuit ROC with a pre-stored fingerprint signal (S5). The pre-stored fingerprint signal may be a fingerprint signal that is pre-registered by the user.

In an embodiment, the locations and sizes of the touch area TA, the emission area EA, and the fingerprint sensing area FSA in the display device DD may be the same or substantially the same as one another, but the present disclosure is not limited thereto. At least one of the touch area TA, the emission area EA, or the fingerprint sensing area FSA may have a different location and/or size from that of the other(s).

Figure 13:
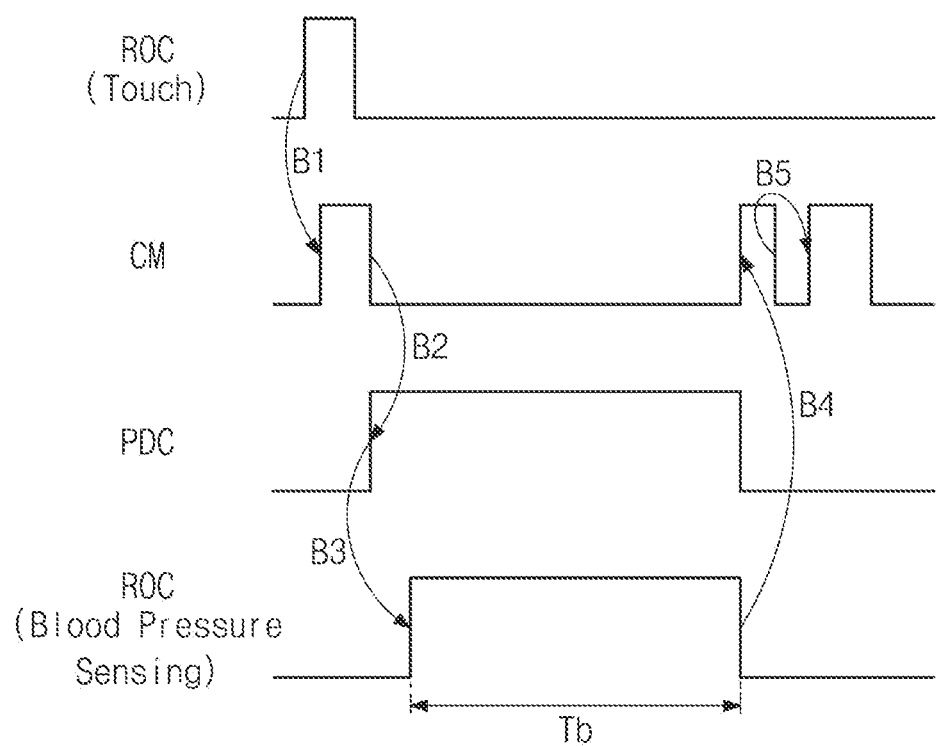
FIG. 13 is a diagram for an operation in a blood pressure sensing mode of a control module of a display device, according to an embodiment of the present disclosure.

FIG. 13 is a diagram for an operation in a blood pressure sensing mode of the control module CM of the display device DD, according to an embodiment of the present disclosure.

Figure 14:
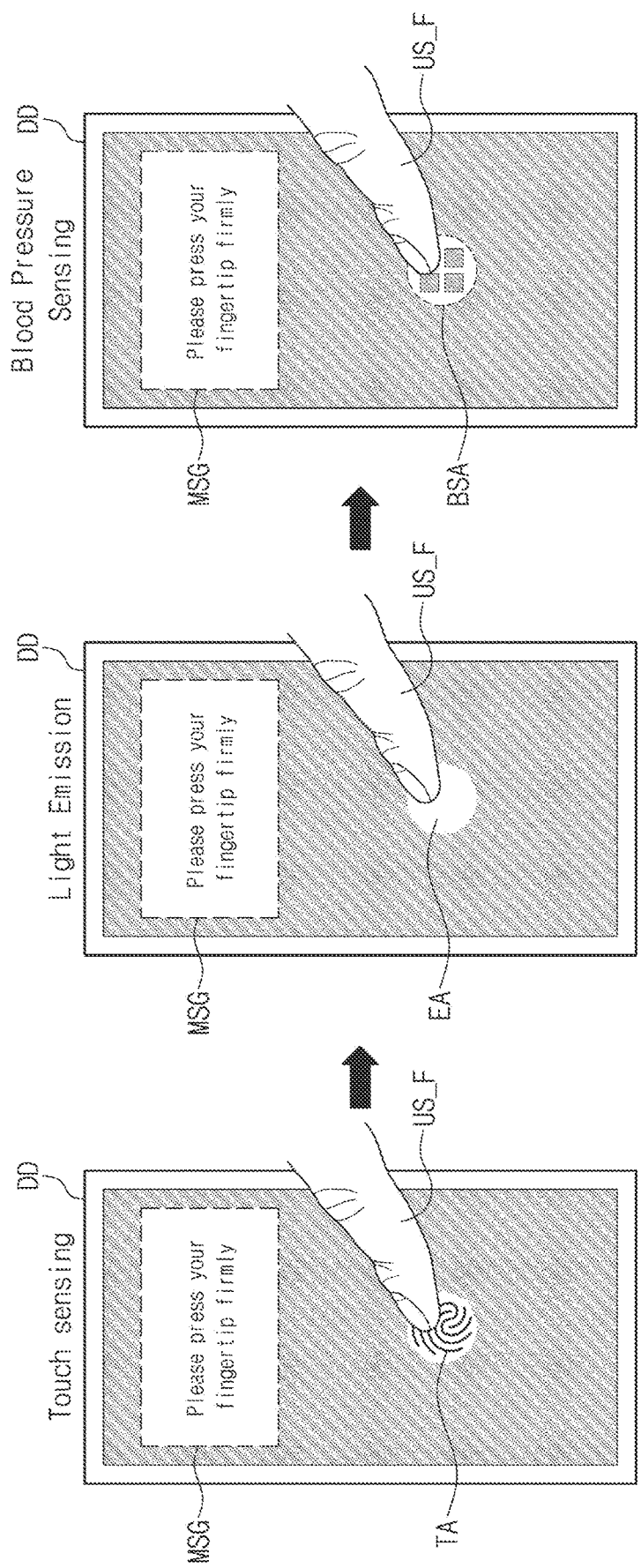
FIG. 14 is a diagram showing an image displayed on a display device in a blood pressure sensing mode.

FIG. 14 is a diagram showing an image displayed on the display device DD in a blood pressure sensing mode.

Referring to FIGS. 10, 13, and 14, the display device DD may operate in a touch sensing process, a light emitting process, and a blood pressure sensing process in the blood pressure sensing mode. In the touch sensing process, when a message MSG saying "please press your fingertip firmly" is displayed at a suitable location (e.g., a predetermined location) on the display device DD, a user may touch the user's finger US_F to a touch area TA of the display device DD. The kind and form of the message MSG displayed on the display device DD may be variously modified as needed or desired.

When the touch by the user's finger US_F is detected by the readout circuit ROC, the control module CM of the display device DD receives the readout signal SS from the readout circuit ROC (B1). In the light emitting process, the control module CM outputs, to the panel driving circuit PDC, the input image signal RGB and the control signal CTRL, which are used to control the luminance of an emission area EA of the display panel DP, in response to the readout signal SS from the readout circuit ROC (B2).

In the blood pressure sensing process, the control module CM outputs the readout control signal RCS for selecting a blood pressure sensing area BSA of the display panel DP to the readout circuit ROC (B3). The readout circuit ROC performs control for sensing a blood pressure from the blood pressure sensing area BSA of the display panel DP in response to the readout control signal RCS from the control module CM.

In an embodiment, during a blood pressure sensing time Tb, the readout circuit ROC may sense the blood pressure from the blood pressure sensing area BSA of the display panel DP. The readout circuit ROC provides the control module CM with the blood pressure sensing signal received from the blood pressure sensing area BSA of the display panel DP (B4).

The control module CM calculates the user's blood pressure based on the blood pressure sensing signal from the readout circuit ROC (B5).

In an embodiment, the locations and sizes of the touch area TA, the emission area EA, and the blood pressure sensing area BSA in the display device DD may be the same or substantially the same as one another, but the present disclosure is not limited thereto. At least one of the touch area TA, the emission area EA, or the blood pressure sensing area BSA may have a different location and/or size from that of the other(s).

In an embodiment, in order for the readout circuit ROC to detect the blood pressure from the blood pressure sensing area BSA of the display panel DP, the blood pressure sensing time Tb may be longer than the fingerprint sensing time Tf. However, the present disclosure is not limited thereto. The blood pressure sensing time Tb and the fingerprint sensing time Tf may be variously modified as needed or desired.

Figure 15A:
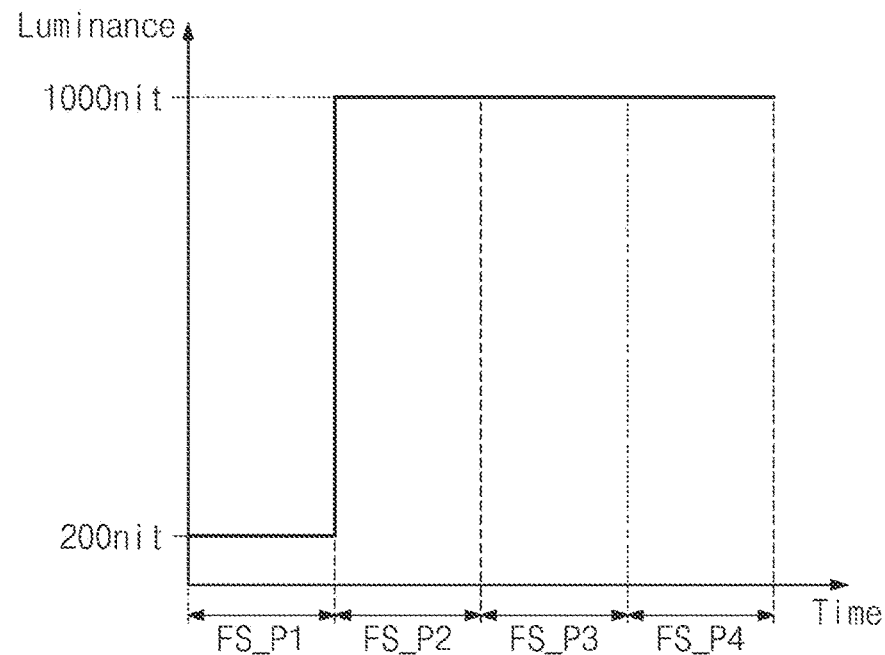
FIGS. 15A-15C are diagrams showing changes in luminance of an emission area in a display device in a fingerprint sensing mode.
Figure 15B:
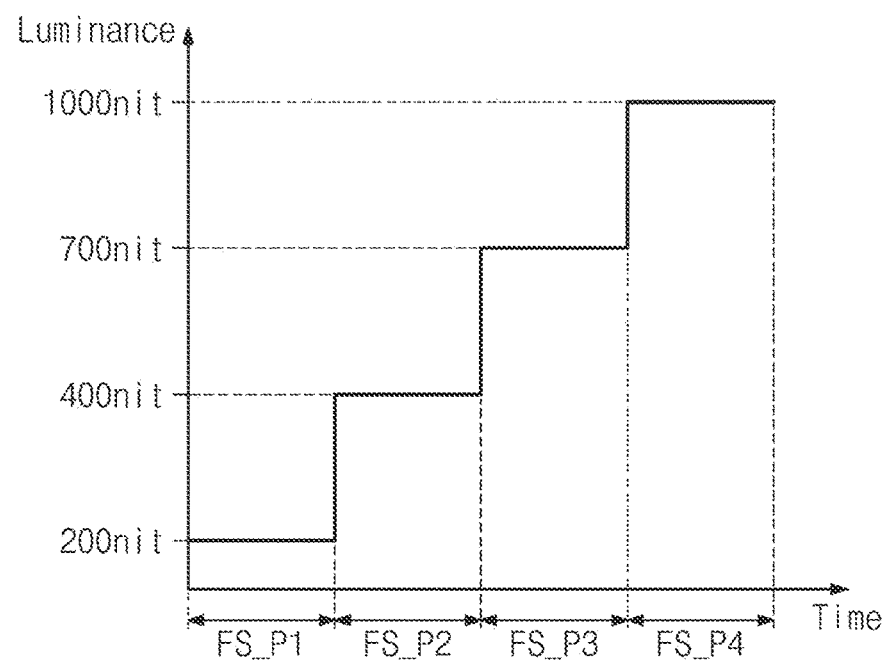
Figure 15C:
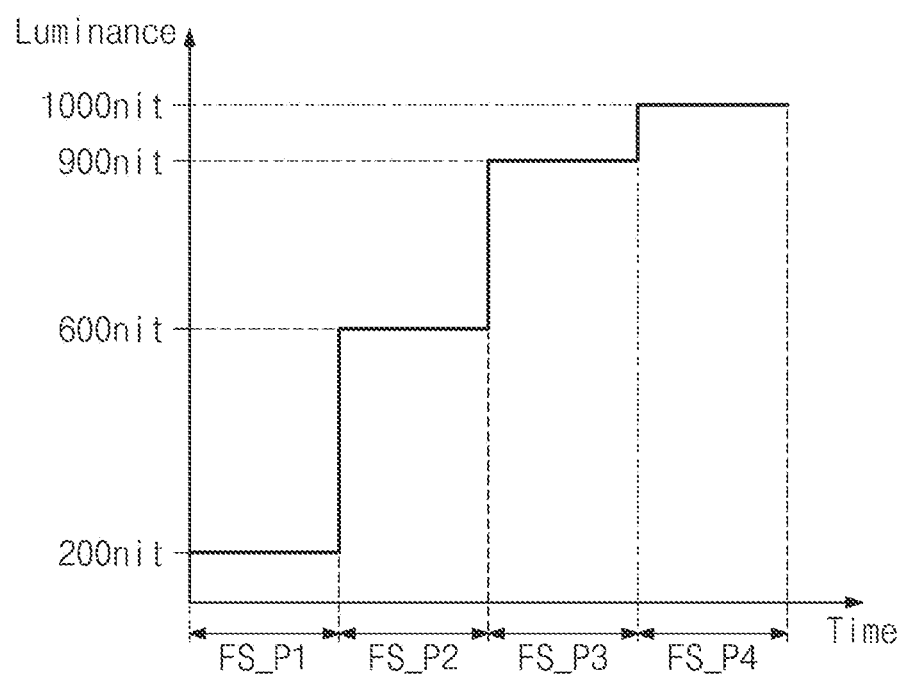

FIGS. 15A, 15B, and 15C are diagrams showing changes in luminance of the emission area EA in the display device DD in a fingerprint sensing mode.

Referring to FIGS. 10, 12, and 15A, when receiving the readout signal SS from the readout circuit ROC in a touch sensing process, the control module CM allows the panel driving circuit PDC to increase the luminance of the emission area EA.

The light sensing element OPD of the sensor FXij shown in FIG. 7 may sense the user's fingerprint information by sensing the amount of light reflected by the user's hand after light is emitted from the display panel DP. As the luminance of light emitted from the display panel DP is increased (e.g., is high), the sensors FX (e.g., see FIG. 3) may more accurately detect a difference in the light reflected by the ridges of a fingerprint and the valleys between the ridges.

As shown in FIG. 15A, in a first emission and fingerprint sensing period FS_P1, the control module CM may control (e.g., may set) the luminance of the emission area EA to a first luminance level (e.g., 200 nits). When the readout signal SS received through the readout circuit ROC does not match a predetermined fingerprint signal, the control module CM may repeatedly perform light emission and fingerprint sensing operations.

In a second emission and fingerprint sensing period FS_P2, the control module CM may control (e.g., may set) the luminance of the emission area EA to a higher or maximum luminance level (e.g., 1000 nits). In a third emission and fingerprint sensing period FS_P3 and a fourth emission and fingerprint sensing period FS_P4, the control module CM may maintain or substantially maintain the luminance of the emission area EA at the higher or maximum luminance level (e.g., 1000 nits).

As shown in FIG. 15B, the control module CM may increase the luminance of the emission area EA step-by-step. For example, in the first emission and fingerprint sensing period FS_P1, the control module CM may step-by-step increase the luminance of the emission area EA to 200 nit. In the second emission and fingerprint sensing period FS_P2, the control module CM may step-by-step increase the luminance of the emission area EA to 400 nit. In the third emission and fingerprint sensing period FS_P3, the control module CM may step-by-step increase the luminance of the emission area EA to 700 nit. In the fourth emission and fingerprint sensing period FS_P4, the control module CM may step-by-step increase the luminance of the emission area EA to 1000 nit. When the luminance of the emission area EA is step-by-step increased in this way, power consumption may be reduced compared to the example shown in FIG. 15A. However, the present disclosure is not limited thereto, and it will be understood that the number of emission and fingerprint sensing periods, a level of the luminance increase of the emission area EA, and the like may be variously modified as needed or desired.

As shown in FIG. 15C, the control module CM may increase the luminance of the emission area EA step-by-step, and the luminance increase width may be set irregularly. In other words, the amount of luminance increase for the different emission and fingerprint sensing periods may vary. For example, in the first emission and fingerprint sensing period FS_P1, the control module CM may step-by-step increase the luminance of the emission area EA to 200 nit. In the second emission and fingerprint sensing period FS_P2, the control module CM may step-by-step increase the luminance of the emission area EA to 600 nit. In the third emission and fingerprint sensing period FS_P3, the control module CM may step-by-step increase the luminance of the emission area EA to 900 nit. In the fourth emission and fingerprint sensing period FS_P4, the control module CM may step-by-step increase the luminance of the emission area EA to 1000 nit.

As shown in FIGS. 15A to 15C, the control module CM may improve the fingerprint sensing performance of the display device DD by increasing the luminance of the emission area EA. In more detail, while minimizing or reducing power consumption by variously changing the luminance of the emission area EA during a fingerprint sensing process, the fingerprint sensing performance of the display device DD may be improved.

Figure 16A:
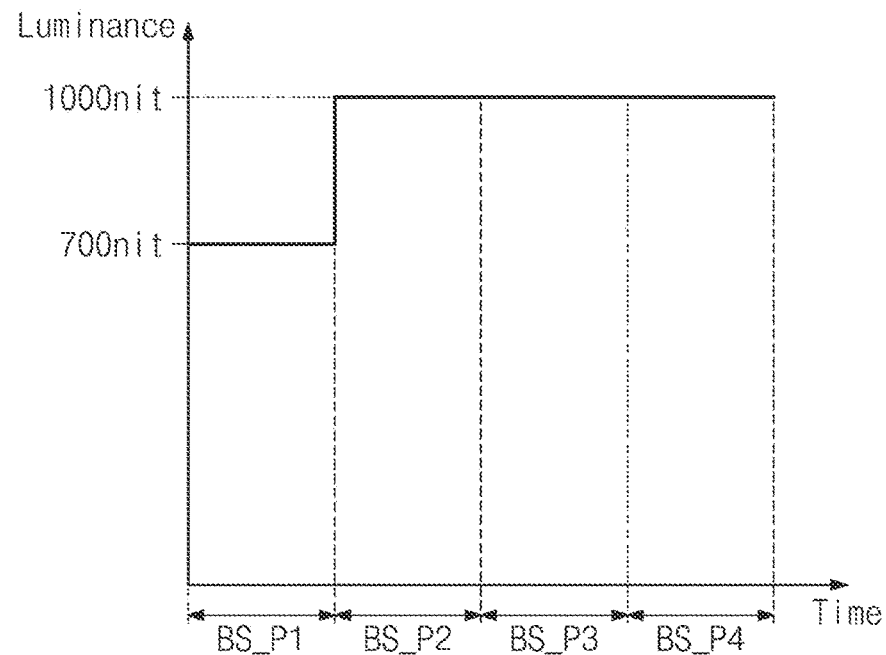
FIGS. 16A and 16B are diagrams showing changes in luminance of an emission area in a display device in a blood pressure sensing mode.
Figure 16B:
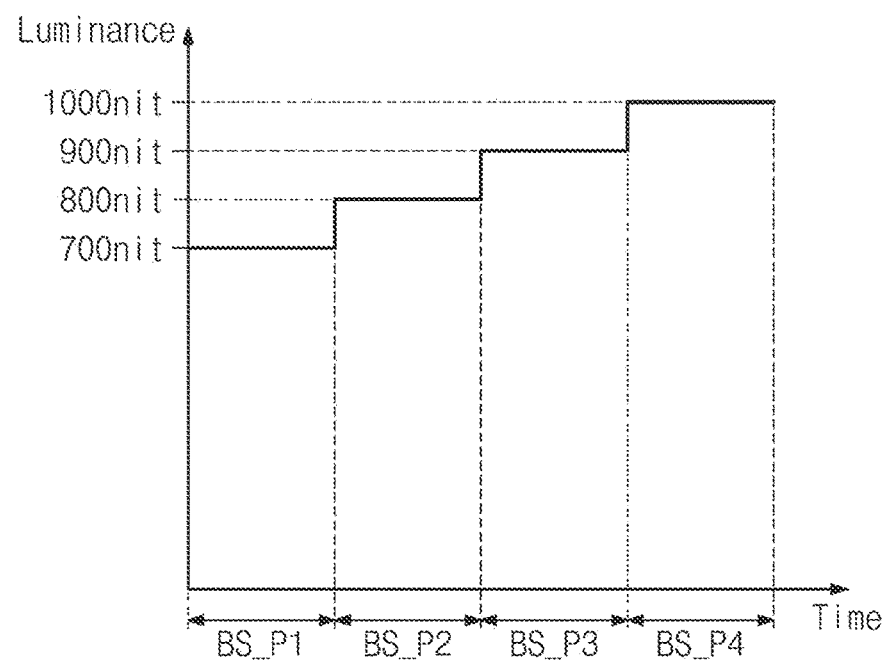

FIGS. 16A and 16B are diagrams showing changes in luminance of the emission area EA in the display device DD in a blood pressure sensing mode.

Referring to FIGS. 10, 14, and 16A, when receiving the readout signal SS from the readout circuit ROC in a touch sensing process, the control module CM allows the panel driving circuit PDC to increase the luminance of the emission area EA.

The light sensing element OPD of the sensor FXij shown in FIG. 7 may sense the user's blood pressure information by sensing the amount of light reflected by the user's hand after light is emitted from the display panel DP. Because a change in systolic and diastolic blood volume of the heart is minute, a change in the amount of reflected light may not be large. As the luminance of the light emitted from the display panel DP is increased (e.g., is high), the performance of the blood pressure sensing according to a difference value of the amount of light reflected from blood vessels may be improved.

As shown in FIG. 16A, in a first emission and blood pressure sensing period BS_P1, the control module CM may control (e.g., may set) the luminance of the emission area EA to a second luminance level (e.g., 700 nits). In an embodiment, the second luminance level is higher than the first luminance level.

When it is difficult to calculate a difference between systole and diastole of the heart based on the readout signal SS received through the readout circuit ROC (e.g., when it is impossible to measure the blood pressure), the control module CM may repeatedly perform emission and blood pressure sensing operations.

In a second emission and blood pressure sensing period BS_P2, the control module CM may control (e.g., may set) the luminance of the emission area EA to the higher or maximum luminance level (e.g., 1000 nits). In an embodiment, the higher or maximum luminance level is higher than the second luminance level.

In a third emission and blood pressure sensing period BS_P3 and a fourth emission and blood pressure sensing period BS_P4, the control module CM may maintain the luminance of the emission area EA at the higher or maximum luminance level (e.g., 1000 nits).

As shown in FIG. 16B, the control module CM may increase the luminance of the emission area EA step-by-step. For example, in the first emission and blood pressure sensing period BS_P1, the control module CM may step-by-step increase the luminance of the emission area EA to 700 nit. In the second emission and blood pressure sensing period BS_P2, the control module CM may step-by-step increase the luminance of the emission area EA to 800 nit. In the third emission and blood pressure sensing period BS_P3, the control module CM may step-by-step increase the luminance of the emission area EA to 900 nit. In the fourth emission and blood pressure sensing period BS_P4, the control module CM may step-by-step increase the luminance of the emission area EA to 1000 nit. When the luminance of the emission area EA is step-by-step increased in this way, power consumption may be reduced compared to the example shown in FIG. 16A. However, the present disclosure is not limited thereto, and it will be understood that the number of emission and blood pressure sensing periods, a level of the luminance increase of the emission area EA, and the like may be variously modified as needed or desired.

Figure 17:
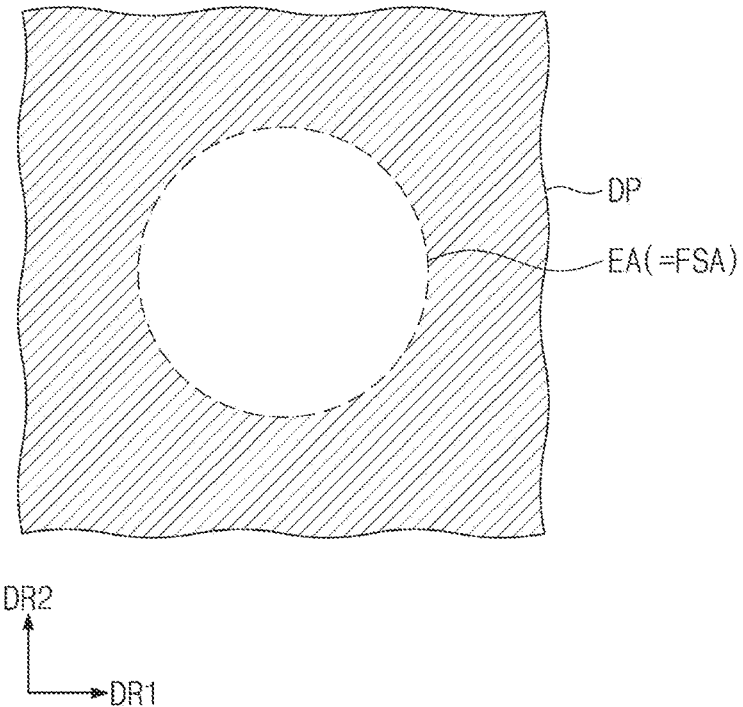
FIG. 17 is a diagram showing an emission area and a fingerprint sensing area of a display panel in a fingerprint sensing mode.

FIG. 17 is a diagram showing the emission area EA and the fingerprint sensing area FSA of the display panel DP in a fingerprint sensing mode.

Referring to FIGS. 10, 12, and 17, in a light emitting process of a fingerprint sensing mode, the control module CM may increase the luminance of the emission area EA of the display panel DP. The readout circuit ROC may sense a fingerprint from the fingerprint sensing area FSA of the display panel DP.

In an embodiment, the emission area EA and the fingerprint sensing area FSA of the display panel DP may be circular. In an embodiment, the locations, shapes, and sizes of the emission area EA and the fingerprint sensing area FSA of the display panel DP may be the same as each other.

Figure 18:
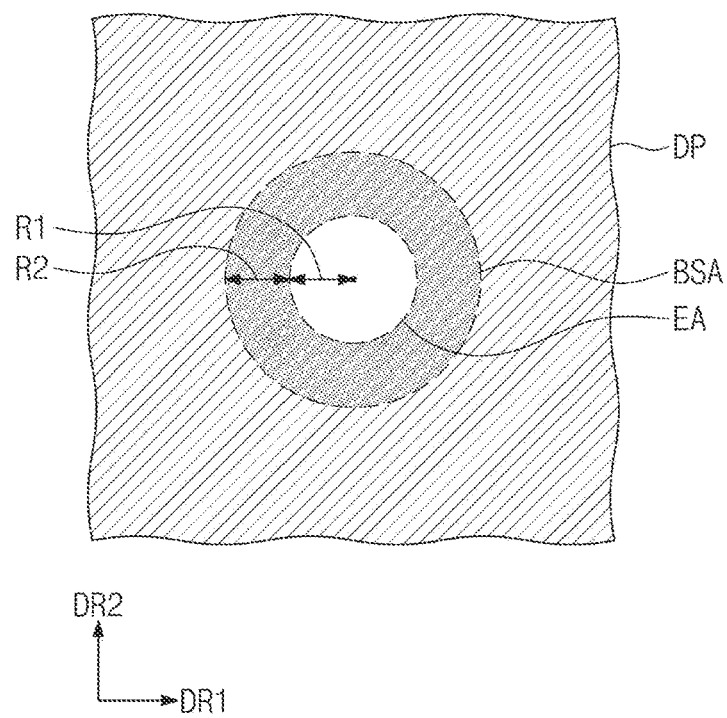
FIG. 18 is a diagram showing an emission area and a blood pressure sensing area of a display panel in a blood pressure sensing mode.

FIG. 18 is a diagram showing the emission area EA and the blood pressure sensing area BSA of the display panel DP in a blood pressure sensing mode.

Referring to FIGS. 10, 12, and 18, in a light emitting process of a blood pressure sensing mode, the control module CM may increase the luminance of the emission area EA of the display panel DP. The readout circuit ROC may sense blood pressure from the blood pressure sensing area BSA of the display panel DP.

In an embodiment, the emission area EA of the display panel DP may be circular, and the blood pressure sensing area BSA may have a ring shape surrounding (e.g., around a periphery of) the emission area EA.

In an embodiment, a radius R1 of the emission area EA may be 3 to 4 mm. In an embodiment, a width R2 of the blood pressure sensing area BSA in the first direction DR1 may be 3 to 4 mm. However, the present disclosure is not limited thereto, and the radius R1 of the emission area EA of the display panel DP and the width R2 of the blood pressure sensing area BSA may be variously modified as needed or desired.

After light output from the emission area EA of the display panel DP reaches a blood vessel located under a dermal layer of a user's skin and is reflected, the reflected light is received by the light sensing element OPD (e.g., see FIG. 7). The emission area EA and the blood pressure sensing area BSA may be arranged to not overlap with each other in consideration of an incident angle at which light emitted from the emission area EA reaches the blood vessel, and an angle of reflection of the light reflected from the blood vessel. However, the present disclosure is not limited thereto. For example, the emission area EA and the blood pressure sensing area BSA may partially overlap with each other.

Figure 19:
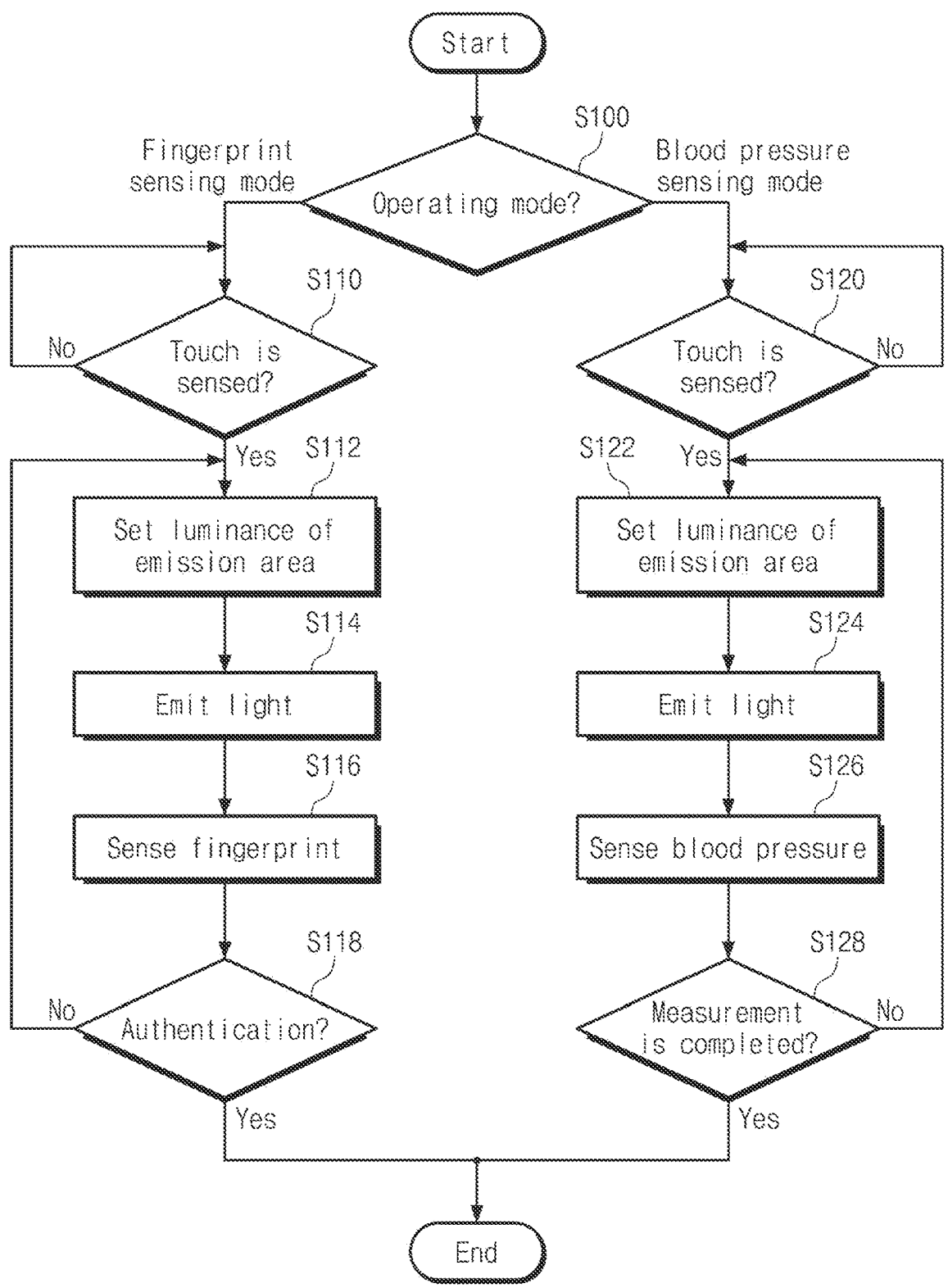
FIG. 19 is a flowchart for an operation of a display device, according to an embodiment of the present disclosure.

FIG. 19 is a flowchart for an operation of a display device, according to an embodiment of the present disclosure.

Referring to FIGS. 10, 12, and 19, the control module CM detects an operating mode (operation S100). In an embodiment, the operating mode may be determined depending on an application program running on the display device DD.

When it is determined that the operating mode is a fingerprint sensing mode, the control module CM determines whether or not there is a touch input from a user (operation S110).

When it is determined from the readout signal SS received from the readout circuit ROC that there is a touch input from the user, the control module CM sets (e.g., controls) the luminance of the emission area EA (operation S112).

As shown in FIG. 15A, in the first emission and fingerprint sensing period FS_P1, the control module CM may control (e.g., may set) the luminance of the emission area EA to a first luminance level (e.g., 200 nits).

When the control module CM provides the panel driving circuit PDC with the input image signal RGB and the control signal CTRL, which are used to control the luminance of the emission area EA, the emission area EA of the display panel DP may emit light at the first luminance level (e.g., 200 nit) (operation S114).

When the user's finger US_F touches the fingerprint sensing area FSA of the display panel DP, the user's fingerprint is sensed by the sensors FX (e.g., see FIG. 3), and the readout circuit ROC provides the readout signal SS to the control module CM (operation S116).

The control module CM performs an authentication process by comparing the readout signal SS received from the readout circuit ROC with a pre-stored fingerprint signal (operation S118). When the readout signal SS matches the pre-stored fingerprint signal, the control module CM determines that fingerprint authentication has passed. When the readout signal SS does not match the pre-stored fingerprint signal, the control module CM returns control to operation S112 to change the luminance of the emission area EA.

The control module CM may change the luminance of the emission area EA according to one of the methods shown in FIGS. 15A, 15B, and 15C. In other words, until the readout signal SS matches the pre-stored fingerprint signal, the control module CM may sequentially perform the operations of the first to fourth emission and fingerprint sensing periods FS_P1, FS_P2, FS_P3, and FS_P4.

When the readout signal SS does not match the pre-stored fingerprint signal even after the operation of the fourth emission and fingerprint sensing period FS_P4 is performed, the control module CM determines that fingerprint authentication fails.

FIGS. 12 and 19 show that the control module CM performs the touch sensing operation (e.g., S110) at the start of a fingerprint sensing mode, but the present disclosure is not limited thereto. When the fingerprint sensing mode starts, the control module CM may perform (e.g., may directly perform) operation S112 of setting (e.g., controlling) the luminance of the emission area EA without performing the touch sensing operation S110.

Referring to FIGS. 10, 14, and 19, when it is determined that the operating mode is a blood pressure sensing mode, the control module CM determines whether or not there is a touch input from a user (operation S120).

When it is determined from the readout signal SS received from the readout circuit ROC that there is a touch input from the user, the control module CM sets (e.g., controls) the luminance of the emission area EA (operation S122).

As shown in FIG. 16A, in the first emission and blood pressure sensing period BS_P1, the control module CM may control (e.g., may set) the luminance of the emission area EA to a first luminance level (e.g., 700 nits).

When the control module CM provides the panel driving circuit PDC with the input image signal RGB and the control signal CTRL, which are used to control the luminance of the emission area EA, the emission area EA of the display panel DP may emit light at the first luminance level (e.g., 700 nit) (operation S124).

When the user's finger US_F touches the blood pressure sensing area BSA of the display panel DP, the user's blood pressure is sensed by the sensors FX (e.g., see FIG. 3), and the readout circuit ROC provides the readout signal SS to the control module CM (operation S126).

The control module CM measures the user's blood pressure based on the readout signal SS received from the readout circuit ROC (operation S128). When the user's blood pressure is capable of being measured based on the readout signal SS, the control module CM terminates the blood pressure measurement operation. When it is difficult (e.g., it is impossible) to measure the user's blood pressure based on the readout signal SS, the control module CM returns control to operation S122 to change the luminance of the emission area EA.

The control module CM may change the luminance of the emission area EA according to one of the methods shown in FIGS. 16A and 16B. In other words, until the user's blood pressure is capable of being measured based on the readout signal SS, the control module CM may sequentially perform operations of the first to fourth emission and fingerprint sensing periods BS_P1, BS_P2, BS_P3, and BS_P4.

When the user's blood pressure is incapable of being measured based on the readout signal SS even after the operation of the fourth emission and blood pressure sensing period BS_P4 is performed, the control module CM determines that the user's blood pressure is incapable of being measured, and terminates the blood pressure sensing mode.

FIGS. 14 and 19 show that the control module CM performs the touch sensing operation S120 at the start of a blood pressure sensing mode, but the present disclosure is not limited thereto. When the blood pressure sensing mode starts, the control module CM may perform (e.g., may directly perform) operation S122 of setting (e.g., controlling) the luminance of the emission area EA without performing the touch sensing operation S120.

Although some embodiments of the present disclosure have been described for illustrative purposes, those skilled in the art will appreciate that various modifications and substitutions are possible, without departing from the scope and spirit of the present disclosure as disclosed in the accompanying claims and their equivalents.

According to one or more embodiments of the present disclosure, a display device may detect not only a fingerprint, but also biometric information such as a user's blood pressure. Moreover, the display device may detect an external input (e.g., a user's touch). Accordingly, the display device may not include a separate input sensing layer for sensing the external input. In this case, the thickness of the display device may be reduced. As a result, flexibility may be improved, and thus, the display device may be implemented in various suitable ways and kinds. For example, the display device may be implemented as a foldable, rollable, or slidable display device as described above.

According to one or more embodiments of the present disclosure, when sensing the biometric information such as a user's blood pressure, the display device increases the luminance of an image displayed in a sensing area or a peripheral area adjacent to the sensing area. Accordingly, the biometric information detection performance of the display device may be improved.

The electronic or electric devices and/or any other relevant devices or components according to embodiments of the present disclosure described herein (e.g., the control module) may be implemented utilizing any suitable hardware, firmware (e.g. an application-specific integrated circuit), software, or a combination of software, firmware, and hardware. For example, the various components of these devices may be formed on one integrated circuit (IC) chip or on separate IC chips. Further, the various components of these devices may be implemented on a flexible printed circuit film, a tape carrier package (TCP), a printed circuit board (PCB), or formed on one substrate. Further, the various components of these devices may be a process or thread, running on one or more processors, in one or more computing devices, executing computer program instructions and interacting with other system components for performing the various functionalities described herein. The computer program instructions are stored in a memory which may be implemented in a computing device using a standard memory device, such as, for example, a random access memory (RAM). The computer program instructions may also be stored in other non-transitory computer readable media such as, for example, a CD-ROM, flash drive, or the like. Also, a person of skill in the art should recognize that the functionality of various computing devices may be combined or integrated into a single computing device, or the functionality of a particular computing device may be distributed across one or more other computing devices without departing from the spirit and scope of the example embodiments of the present disclosure.

The foregoing is illustrative of some embodiments of the present disclosure, and is not to be construed as limiting thereof. Although some embodiments have been described, those skilled in the art will readily appreciate that various modifications are possible in the embodiments without departing from the spirit and scope of the present disclosure. It will be understood that descriptions of features or aspects within each embodiment should typically be considered as available for other similar features or aspects in other embodiments, unless otherwise described. Thus, as would be apparent to one of ordinary skill in the art, features, characteristics, and/or elements described in connection with a particular embodiment may be used singly or in combination with features, characteristics, and/or elements described in connection with other embodiments unless otherwise specifically indicated. Therefore, it is to be understood that the foregoing is illustrative of various example embodiments and is not to be construed as limited to the specific embodiments disclosed herein, and that various modifications to the disclosed embodiments, as well as other example embodiments, are intended to be included within the spirit and scope of the present disclosure as defined in the appended claims, and their equivalents.

What is claimed is:

1. A display device comprising:
    a display panel comprising:
        a plurality of pixels, each of the plurality of pixels including a light emitting element; and
        a plurality of sensors, each of the plurality of sensors including a light sensing element;
    a panel driving circuit configured to drive the plurality of pixels;
    a readout circuit configured to receive a sensing signal from the plurality of sensors; and
    a controller configured to control the panel driving circuit and the readout circuit,
    wherein the controller is configured to:
        control the panel driving circuit to set a luminance of pixels in an emission area from among the plurality of pixels to a first luminance level in a fingerprint sensing mode; and
        control the panel driving circuit to set the luminance of the pixels in the emission area to a second luminance level in a blood pressure sensing mode, and
    wherein the second luminance level is higher than the first luminance level.

2. The display device of claim 1, wherein, during a first emission and blood pressure sensing period of the blood pressure sensing mode, the controller is configured to measure a blood pressure of a user based on a readout signal received from the readout circuit.

3. The display device of claim 2, wherein, when the blood pressure cannot be sufficiently measured based on the readout signal during the first emission and blood pressure sensing period, the controller is configured to change the luminance of the pixels in the emission area to a luminance level higher than the second luminance level during a second emission and blood pressure sensing period of the blood pressure sensing mode.

4. The display device of claim 3, wherein, during the second emission and blood pressure sensing period of the blood pressure sensing mode, the controller is configured to measure the blood pressure of the user based on the readout signal received from the readout circuit.

5. The display device of claim 1, wherein, during a first emission and fingerprint sensing period of the fingerprint sensing mode, the controller is configured to perform an authentication process by comparing a readout signal received from the readout circuit with a pre-stored fingerprint signal.

6. The display device of claim 5, wherein, when the readout signal does not match the pre-stored fingerprint signal, the controller is configured to change the luminance of the pixels in the emission area into a luminance level higher than the first luminance level of the first emission and fingerprint sensing period.

7. The display device of claim 1, wherein, during a fingerprint sensing time in the fingerprint sensing mode, the readout circuit is configured to receive a sensing signal from sensors in a fingerprint sensing area from among the plurality of sensors,
    wherein, during a blood pressure sensing time in the blood pressure sensing mode, the readout circuit is configured to receive the sensing signal from sensors in a blood pressure sensing area from among the plurality of sensors, and
    wherein the blood pressure sensing time is longer than the fingerprint sensing time.

8. The display device of claim 1, wherein, during the fingerprint sensing mode, the controller is configured to receive a sensing signal from sensors in a fingerprint sensing area from among the plurality of sensors, and
    wherein, during the blood pressure sensing mode, the controller is configured to receive the sensing signal from sensors in a blood pressure sensing area from among the plurality of sensors.

9. The display device of claim 8, wherein, in the fingerprint sensing mode, sizes and shapes of the emission area and the fingerprint sensing area are the same as each other.

10. The display device of claim 8, wherein, in the blood pressure sensing mode, sizes and shapes of the emission area and the blood pressure sensing area are different from each other.

11. The display device of claim 8, wherein, in the blood pressure sensing mode, the emission area has a circle shape having a radius, and the blood pressure sensing area has a ring shape surrounding the emission area.

12. The display device of claim 1, wherein each of the plurality of sensors further comprises:
    a first transistor connected between a reset voltage line and a first sensing node;
    a second transistor connected between a sensor driving voltage line and a second sensing node, and including a gate electrode connected to the first sensing node; and
    a third transistor connected between the second sensing node and a readout line, and including a gate electrode configured to receive a sensor scan signal.

13. The display device of claim 1, wherein the display panel further comprises:
    a base layer;
    a circuit layer on the base layer; and
    an element layer on the circuit layer, and including the light emitting element and the light sensing element.

14. A display device comprising:
    a display panel including:
        a plurality of pixels, each of the plurality of pixels including a light emitting element; and
        a plurality of sensors, each of the plurality of sensors including a light sensing element;
    a panel driving circuit configured to drive the plurality of pixels;
    a readout circuit configured to receive a sensing signal from the plurality of sensors; and
    a controller configured to control the panel driving circuit and the readout circuit,
    wherein the controller is configured to:
        control the panel driving circuit to set a luminance of pixels in an emission area from among the plurality of pixels to a luminance level in a blood pressure sensing mode; and
        control the readout circuit to receive a sensing signal from sensors in a blood pressure sensing area from among the plurality of sensors, and wherein sizes and shapes of the emission area and the blood pressure sensing area are different from each other.

15. The display device of claim 14, wherein, in the blood pressure sensing mode, the emission area has a circle shape having a radius, and the blood pressure sensing area is a ring shape surrounding the emission area.

16. The display device of claim 14, wherein the controller is configured to control the panel driving circuit to set the luminance of the pixels in the emission area to a first luminance level in a fingerprint sensing mode, and control the panel driving circuit to set the luminance of the pixels in the emission area to a second luminance level in a blood pressure sensing mode, and
wherein the second luminance level is higher than the first luminance level.

17. An operating method of a display device including a display panel including a plurality of pixels and a plurality of sensors, the method comprising:
determining an operating mode from among a fingerprint sensing mode and a blood pressure sensing mode;
controlling a luminance of pixels in an emission area from among the plurality of pixels to a first luminance level, when the operating mode is the fingerprint sensing mode; and
controlling the luminance of the pixels in the emission area to a second luminance level, when the operating mode is the blood pressure sensing mode,
wherein the second luminance level is higher than the first luminance level.

18. The method of claim 17, further comprising:
authenticating a fingerprint based on a signal received from sensors in a fingerprint sensing area from among the plurality of sensors, when the operating mode is the fingerprint sensing mode; and
measuring blood pressure of a user based on a signal received from sensors in a blood pressure sensing area from among the plurality of sensors, when the operating mode is the blood pressure sensing mode.

19. The method of claim 18, further comprising changing the luminance of the pixels in the emission area to a level higher than the second luminance level, when the blood pressure of the user cannot be sufficiently measured based on the signal received from the sensors in the blood pressure sensing area.

20. The method of claim 18, wherein sizes and shapes of the emission area and the blood pressure sensing area are different from each other.

* * * * *